United States Patent
Aki et al.

(10) Patent No.: US 11,999,724 B2
(45) Date of Patent: Jun. 4, 2024

(54) METHOD FOR PRODUCING DIARYLPYRIDINE DERIVATIVES

(71) Applicant: Daiichi Sankyo Company, Limited, Tokyo (JP)

(72) Inventors: Yuichi Aki, Tokyo (JP); Fumihiko Toriyama, Tokyo (JP); Natsuki Sakurai, Tokyo (JP); Ai Kameda, Tokyo (JP); Tomokazu Ogura, Tokyo (JP)

(73) Assignee: Daiichi Sankyo Company, Limited, Tokyo (JP)

(*) Notice: Subject to any disclaimer, the term of this patent is extended or adjusted under 35 U.S.C. 154(b) by 750 days.

(21) Appl. No.: 17/252,469

(22) PCT Filed: Jul. 3, 2019

(86) PCT No.: PCT/JP2019/026395
§ 371 (c)(1),
(2) Date: Dec. 15, 2020

(87) PCT Pub. No.: WO2020/009132
PCT Pub. Date: Jan. 9, 2020

(65) Prior Publication Data
US 2021/0188823 A1   Jun. 24, 2021

(30) Foreign Application Priority Data
Jul. 4, 2018   (JP) .................... 2018-127197

(51) Int. Cl.
| C07D 405/14 | (2006.01) |
| B01J 23/44 | (2006.01) |
| C07D 319/12 | (2006.01) |
| C07D 405/12 | (2006.01) |

(52) U.S. Cl.
CPC ............ *C07D 405/14* (2013.01); *B01J 23/44* (2013.01); *C07D 319/12* (2013.01); *C07D 405/12* (2013.01)

(58) Field of Classification Search
None
See application file for complete search history.

(56) References Cited

U.S. PATENT DOCUMENTS

| 8,933,103 B2 | 1/2015 | Ohki et al. |
| 11,208,403 B2 | 12/2021 | Haginoya et al. |

FOREIGN PATENT DOCUMENTS

| CN | 106604920 | 4/2017 | |
| EP | 2810937 | 12/2014 | |
| EP | 3168219 | 5/2017 | |
| EP | 3603638 | 2/2020 | |
| WO | WO 2013/115280 | 8/2013 | |
| WO | WO2016006706 | 1/2016 | |
| WO | WO-2016006706 A1 * | 1/2016 | ........... A61K 31/444 |
| WO | WO2018174219 | 9/2018 | |

OTHER PUBLICATIONS

Office Action in Japanese Appln. No. 2020-529019, dated May 9, 2023, 5 pages (with English translation).
International Preliminary Report on Patentability in International Appln. No. PCT/JP2019/026395, dated Jan. 5, 2021, 10 pages.
Office Action in Taiwanese Appln. No. 108123125, dated Aug. 29, 2023, 9 pages (with English translation).
Church et al., "New Synthetic Routes to 3-, 5-, and 6-Aryl-2-chloropyridines", Journal of Organic Chemistry, 1995, 60(12):3750-3758.
Ege et al., "A new synthesis of 4-(dimethylamino)-1, 3-butadiene-1, 1-dicarbonitriles and their cyclization to 2-amino-3-cynapyridines", Synthesis, 1979, 5:376-378.
International Search Report in International Appln. No. PCT/JP2019/026395, dated Sep. 17, 2019, 4 pages with English Translation.
Juhasz et al., "Synthesis and glycogen phosphorylase inhibitor activity of 2, 3-dihydrobenzo [1,4] dioxin derivatives", Bioorganic & Medicinal Chemistry, 2007, 15(12):4048-4056.
Villemin et al., "Solvent-less convenient synthesis of new cyano-2-aminopyridine derivatives from enamino nitriles", Tetrahedron Letters, 2013, 54(13):1664-1668.
Examination Report in Indian Appln. No. 202017055646, dated Jul. 1, 2022, 6 pages.
Palucki et al., "Profiling the Formation of 2-Chloro-N,N-dimethylamino Trimethinium Chloride Salt, a Key Intermediate in the Manufacturing Process of Etoricoxib," Org. Proc. Res. Dev., Jan. 2005, 9(2):141-148.
Sofan et al., "Studies on 1,3-indandione: Synthesis of Fluorenones and Indeno(2,1-c)pyridazine," Journal für Praktische Chemie, 1990, 332(5):640-644.
European Extended Search Report in EP Appln. No. 19831009.6, dated May 11, 2021, 8 pages.

* cited by examiner

Primary Examiner — Jeffrey S Lundgren
Assistant Examiner — Michael J Schmitt
(74) Attorney, Agent, or Firm — Fish & Richardson P.C.

(57) ABSTRACT

The present invention relates to a novel method for producing diarylpyridine derivatives, and the object of the present invention is to provide a novel, industrially useful method. The present inventors developed a novel method for synthesizing pyridine rings without using palladium, a strong base, or a high-temperature reaction. In particular, they successfully developed a method that can be used to synthesize iminium salts as intermediates, synthesize cyano compounds from these iminium salts, and cyclize the cyano compounds into pyridines under very mild reaction conditions.

18 Claims, 1 Drawing Sheet

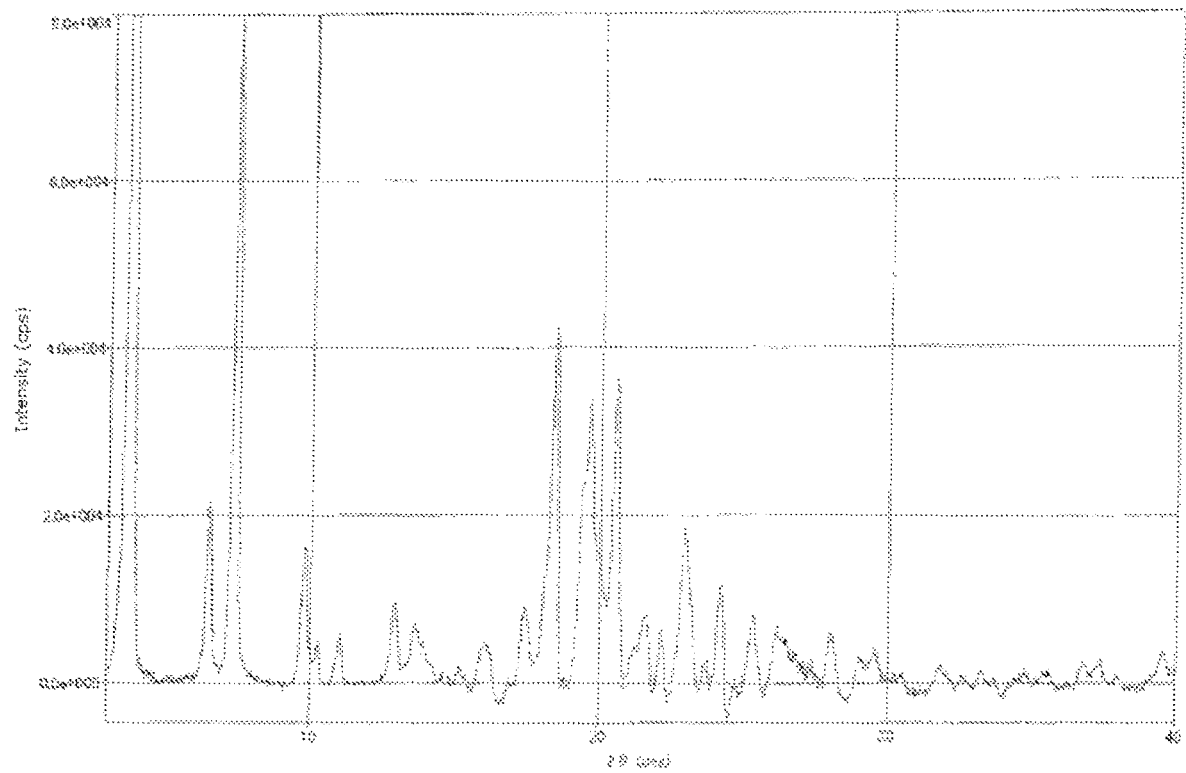

METHOD FOR PRODUCING DIARYLPYRIDINE DERIVATIVES

CROSS-REFERENCE TO RELATED APPLICATIONS

This application is a U.S. national phase filing under 35 U.S.C. § 371 of International Application No. PCT/JP2019/026395, filed Jul. 3, 2019, which claims priority to Japanese Application No. 2018-127197, filed Jul. 4, 2018. The entire contents of the prior applications are incorporated herein by reference in their entirety.

TECHNICAL FIELD

The present invention relates to a novel method for producing diarylpyridine derivatives and, more specifically, to a production method including a novel method for synthesizing pyridine rings without using palladium.

BACKGROUND ART

Diarylpyridine derivatives are known to be useful as pharmaceuticals or materials for producing pharmaceuticals, and to be useful for treating tumors (Patent Document 1).

Patent Document 1 discloses several diarylpyridine derivatives and a production method for these diarylpyridine derivatives. In the diarylpyridine derivative production method disclosed in this document, halogen atom-substituted pyridine derivatives are used as starting compounds and an aryl group is introduced to the pyridine ring by performing a coupling reaction using palladium (see, for example, intermediate 9a and intermediate 10a in the examples). However, halogen atom-substituted pyridine derivatives are expensive, and the repeated use of palladium means attention has to be paid to residual palladium in the target product.

In known methods for synthesizing pyridine rings without the use of palladium, Compound (A) below is used as a starting compound,

[Formula 1]

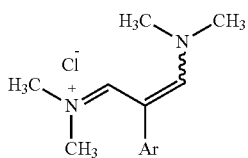

(A)

Compound A is cyanated to synthesize Compound below,

[Formula 2]

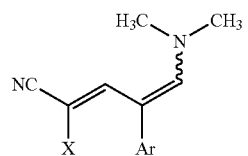

(B)

Compound B is cyclized by reacting it with a compound having an amino group such as ammonia to synthesize a pyridine ring (Non-Patent Documents 1, 2 and 3).

However, a reaction using a strong base at ultra-low temperatures (Non-Patent Document 1) or a reaction at high temperatures (Non-Patent Documents 3, 4) is required to synthesize Compound A. Also, the conversion reaction from Compound A to Compound B has to be conducted in the presence of a strong base (Non-Patent Documents 2, 3), the cyclization of compound B has to be conducted under high-temperature conditions (Non-Patent Documents 1, 2), a large amount of strong base needs to be present (Non-Patent Document 2), or both (Non-Patent Document 3). All of these are difficult to carry out.

PRIOR ART DOCUMENTS

Patent Documents

Patent Document 1: WO 2016006706 A1

Non-Patent Documents

Non-Patent Document 1: Synthesis Issue 05, 1979, 376
Non-Patent Document 2: J. Prakt. Chem., 5, 1990, 332
Non-Patent Document 3: J. Org. Chem. 60, 1995, 3750
Non-Patent Document 4: Org. Proc. Res. Dev., Vol. 9, No. 2, 2005, 141

SUMMARY OF THE INVENTION

Problem to be Solved by the Invention

The present invention relates to a novel method for producing diarylpyridine derivatives, and the object of the present invention is to provide a novel, industrially useful method for synthesizing pyridine rings without using palladium, a strong base, or a high-temperature reaction.

Means for Solving the Problem

The present invention relates to (1) to (13) below.

(1) A production method comprising the step of reacting a compound represented by Formula (I):

[Formula 3]

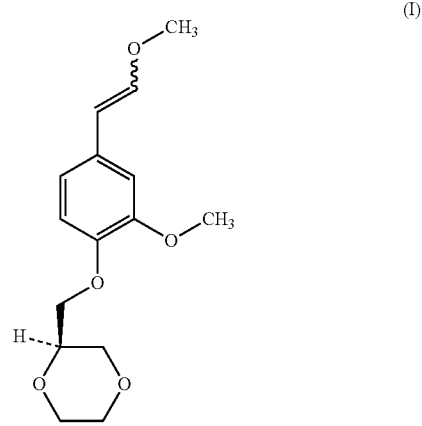 [SMILES: COC=Cc1ccc(OC[C@H]2COCCO2)c(OC)c1]

(I)

with a chlorinating agent and dimethylformamide to obtain a compound represented by Formula (II):

[Formula 4]

(II)

or a salt thereof.

(2) A production method according to (1), wherein the chlorinating agent is oxalyl chloride.

(3) A production method comprising the steps of producing a compound represented by Formula (II) using a production method according to (1) or (2), and reacting the compound with a compound represented by Formula (III):

[Formula 5]

(III)

in the presence of a base to obtain a compound represented by Formula (IV):

[Formula 6]

(IV)

or a salt thereof.

(4) A production method according to (3), wherein the base is 2,6-lutidine.

(5) A production method comprising the steps of producing a compound represented by Formula (IV) or salt thereof using a production method according to (3) or (4), and reacting the compound with benzylamine to obtain a compound represented by Formula (V):

[Formula 7]

(V)

or a salt thereof.

(6) A production method comprising the steps of: (i) reacting a compound represented by Formula (I') with a Wittig reagent;

[Formula 8]

(I')

(ii) reacting the compound obtained in step (i) with a chlorinating agent and dimethylformamide;
(iii) reacting the compound obtained in step (ii) with a compound represented by Formula (III) above in the presence of a base; and
(iv) reacting the compound obtained in step (iii) with benzylamine to obtain a compound represented by Formula (V) above or a salt thereof.

(7) A method according to (6), wherein the Wittig reagent in step (i) is $Ph_3P(Cl)CH_2OMe$.

(8) A production method according to (6) or (7), wherein the chlorinating agent in step (ii) is oxalyl chloride.

(9) A production method according to any one of (6) to (8), wherein the base in step (iii) is 2,6-lutidine.

(10) A production method comprising the steps of producing a compound represented by Formula (V) or salt thereof using a production method according to any one of (5) to (9), and reacting the compound with hydrogen in solvent and in the presence of a palladium on carbon catalyst to obtain a compound represented by Formula (VI):

[Formula 9]

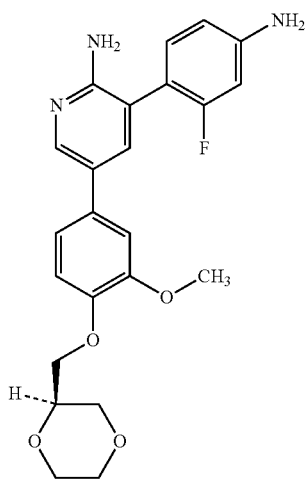

(VI)

or a salt thereof.

(11) A production method according to (10), wherein the compound represented by Formula (V) or salt thereof is a hydrochloric acid salt of a compound represented by Formula (V), and the solvent is 1-propanol or N-methylpyrrolidone.

(12) A production method comprising the steps of producing a compound represented by Formula (VI) or salt thereof using a production method according to (10) or (11), and condensing the compound with a compound represented by Formula (VII):

[Formula 10]

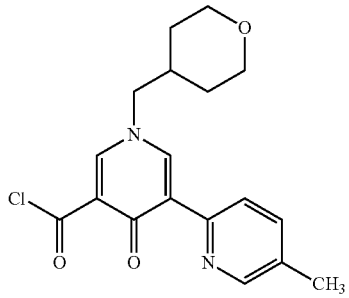

(VII)

or salt thereof to obtain a compound represented by Formula (VIII):

[Formula 11]

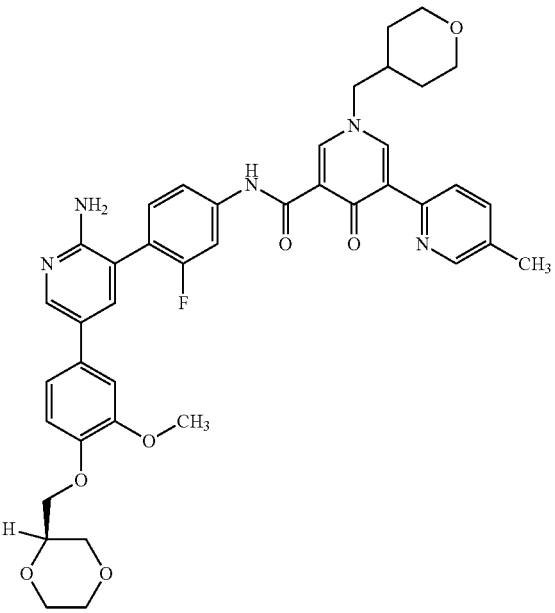

(VIII)

or a salt thereof.

(13) A production method according to (12), wherein the compound represented by Formula (VIII) or salt thereof is a sulfuric acid salt of a compound represented by Formula (VIII).

Another aspect of the production method of the present invention comprises the steps of producing a sulfuric acid salt of a compound represented by Formula (VIII) using a production method according to (13), and crystallizing the salt to obtain crystals of the sulfuric acid salt of the compound represented by Formula (VIII).

In the present invention, the crystals of the sulfuric acid salt of the compound represented by Formula (VIII) have at least five peaks at a diffraction angle (2θ) selected from 3.71±0.2, 6.48±0.2, 7.37±0.2, 9.80±0.2, 10.29±0.2, 11.01±0.2, 18.44±0.2, 20.53±0.2, 22.91±0.2, and 24.15±0.2 in powder X-ray diffraction using CuKα radiation.

Effects of the Invention

The present invention provides a novel method for synthesizing pyridine rings without using palladium, a strong base, or a high-temperature reaction. In particular, the present inventors discovered a method that can be used to synthesize iminium salts, which used to require a reaction using a strong base at ultra-low temperatures or a reaction at high temperatures to synthesize, under very mild reaction conditions, and were able to provide a synthesis method for synthesis of iminium salts into cyano compounds and cyclization to pyridines which does not require a reaction using a strong base or a reaction under high-temperature conditions as in the prior art.

BRIEF DESCRIPTION OF THE DRAWINGS

FIG. 1 is a diagram showing the XRD chart of the compound (26) described in Example 7.

EMBODIMENT OF THE INVENTION

In the present invention, the "chlorinating agent" may be any agent that reacts with dimethylformamide to produce a Vilsmeier reagent. Examples include chlorine, oxalyl chloride, thionyl chloride, and phosphorus oxychloride. Oxalyl chloride is preferred.

In the present invention, the "base" used to produce a compound represented by Formula (IV) or a salt thereof may be any base able to extract the proton at the benzyl position in a compound represented by Formula (III). Examples include 1,8-diazabicyclo [5.4.0] undeca-7-en (DBU), N, N-diisopropylethylamine (DIPEA), 1,4-diazabicyclo[2.2.2]octane (DABCO), triethylamine, pyridine, 2,6-lutidine, N-methylmorpholine, and tetramethylethylenediamine (TMEDA). 2,6-Lutidine and TMEDA are preferred, and 2,6-lutidine is especially preferred.

The "palladium on carbon catalyst" that can be used in the present invention may be any palladium on carbon catalyst that can be used in a debenzylation reaction and in a reduction reaction from a nitro group to an amino group. Examples include M (Kawaken Fine Chemicals), PH (Kawaken Fine Chemicals), PE type (NE Chemcat), and AER type (NE Chemcat). PE type (NE Chemcat) is preferred.

In the present invention, the "solvent" that can be used in the reaction using the palladium on carbon can be, for example, methanol, ethanol, 1-propanol, 1,3-dimethyl-2-imidazolidinone, or N-methylpyrrolidone. 1-Propanol or N-methylpyrrolidone is preferred.

In the present invention, "Wittig reagent" means a reagent that can react with aldehydes and ketones to form carbon-carbon double bonds. A Wittig reagent able to obtain a compound in which an alkoxy group is substituted in a double bond is preferred. Examples include $Ph_3P(Cl)CH_2OMe$, $Ph_3P(Br)CH_2OMe$, and $Ph_3P(I)CH_2OMe$.

In the present invention, compounds represented by Formula (I), compounds represented by Formula (II) or salts thereof, and compounds represented by Formula (IV) or salts thereof include geometric isomers.

In the present invention, compounds represented by Formula (II), compounds represented by Formula (IV), compounds represented by Formula (V), compounds represented by Formula (VI), compounds represented by Formula (VII), and compounds represented by Formula (VIII) can be turned into salts by reacting them with an acid. Examples include hydrohalides such as hydrofluoride, hydrochlorides, hydrobromides, and hydroiodides; inorganic acid salts such as nitrates, perchlorates, sulfates, and phosphates; $C_1$-$C_6$ alkyl sulfonates such as methane sulfonate, trifluoromethane sulfonate, and ethane sulfonate; allyl sulfonates such as benzene sulfonate and p-toluene sulfonate; organic acid salts such as acetates, malates, fumarates, succinates, citrates, ascorbates, tartrates, oxalates, and adipates; and amino acid salts such as glycine salts, lysine salts, arginine salts, ornithine salts, glutamates, and aspartates.

"Salts" in the present invention may be molecules formed via ionic bonds as well as molecules formed via hydrogen bonds and/or van der Waals bonds.

In the present invention, compounds represented by Formula (I), compounds represented by Formula (I'), compounds represented by Formula (II), compounds represented by Formula (III), compounds represented by Formula (IV) or salts thereof, compounds represented by Formula (V) or salts thereof, compounds represented by Formula (VI) or salts thereof, compounds represented by Formula (VII) or salts thereof, and compounds represented by Formula (VIII) or salts thereof may be left in the air or recrystallized to take in water molecules and become hydrates. These hydrates are also included in the present invention.

In the present invention, compounds represented by Formula (I), compounds represented by Formula (I'), compounds represented by Formula (II), compounds represented by Formula (III), compounds represented by Formula (IV) or salts thereof, compounds represented by Formula (V) or salts thereof, compounds represented by Formula (VI) or salts thereof, compounds represented by Formula (VII) or salts thereof, and compounds represented by Formula (VIII) or salts thereof may be left in a solvent or recrystallized to absorb a solvent and become solvates. These solvates are also included in the present invention.

In the present invention, "crystal" refers to a solid whose internal structure is three-dimensionally formed by regular repetition of constituent atoms and molecules, and which is distinguished from an amorphous solid or an amorphous body having no such regular internal structure.

In the present invention, the crystalline form of a compound represented by Formula (VIII) or a salt thereof can be verified by observation under a polarizing microscope or by performing a powder X-ray crystal analysis or a single crystal X-ray diffraction measurement. The type of crystal can be identified by comparing the characteristics of the crystal with data based on indices measured in advance. In a preferred aspect of the present invention, a crystal of the present invention can be confirmed to be a crystal using such measuring means.

In the present invention, crystals having completely matching diffraction angles in powder X-ray diffraction and crystals having matching diffraction angles within a range of ±0.2 are included in the present invention. This is a common practice as there are variations in peak values due to differences in instruments, samples, and sample preparation. Because diffraction angles (2θ) in powder X-ray diffraction may have an error within the range of ±0.2, diffraction angle values need to be understood as including numerical values within the range of about ±0.2.

The following is a description of the present invention. It should be understood that the reaction conditions of the present invention are not limited to those in the following examples. In the present invention, the functional groups in the compounds may be protected by a suitable protecting group. Examples of functional groups include hydroxyl groups, carboxy groups, and amino groups. For types of protecting groups and the conditions for introducing and removing these protecting groups, see Protective Groups in Organic Synthesis (T. W. Green and P. G. M. Wuts, John Wiley & Sons, Inc., New York, 2006).

EXAMPLES

The following is a more detailed description of the present invention with reference to examples, but the scope of the present invention is not limited to these examples.

The abbreviations used in the examples have the following meanings.

mg: milligram, g: gram, kg: kilogram, mL: milliliter, L: liter, mol: mol, MHz: megahertz.

In the examples below, the chemical shift value in the nuclear magnetic resonance (hereinafter, $^1$H NMR: 500

MHZ) spectrum is described as a δ value (ppm) using tetramethylsilane as the reference substance. In the splitting pattern, s indicates a single line, d indicates a double line, t indicates a triple line, q indicates a quadruple line, m indicates a multiple line, and br indicates a broad line.

The measurement conditions for the powder X-ray diffractometer used in the examples are as follows.

Measuring range: 3-40 deg
Step: 0.020 deg
Speed: 10 deg/min
Target: Cu (Kα)
Tube voltage: 40 kV
Tube current: 15 mA
Measurement temperature: Room temperature (25° C.)

Reference Example 1

Production of potassium (5-methylpyridine-2-yl) acetate (2)

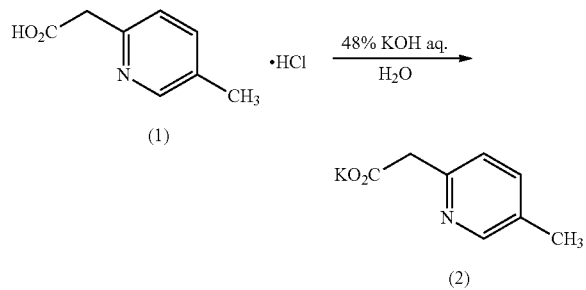

[Formula 12]

Under a nitrogen atmosphere, water (25.7 L) and (5-methylpyridine-2-yl) acetate hydrochloride (1) (19.0 kg, 101 mol) were added to a reaction vessel, and stirred at 0° C. After adding a 48% potassium hydroxide aqueous solution (23.24 kg) while keeping the temperature between −5° C. and 10° C., the pH was adjusted to 12.6 with concentrated hydrochloric acid (0.15 kg). After confirming precipitation of potassium chloride, the contents were stirred at 0° C. for 20 minutes and 1-propanol (143 L) was added dropwise. After completion of the dropwise addition, the temperature was raised to 25° C., and the contents were stirred for 15 minutes and concentrated under reduced pressure until the liquid volume reached 66.5 L. 1-Propanol (143 L) was added dropwise at 20° C., and the contents were concentrated again under reduced pressure until the liquid volume reached 66.5 L. Then, 1-propanol (143 L) was added dropwise at 25° C., hot filtration was performed at 50° C., and contents were washed with 1-propanol (57 L) at 50° C. to remove insoluble matter. The resulting filtrate was concentrated under reduced pressure until the liquid volume reached 95 L, and a 1-propanol aqueous solution (1-propanol 19 L, water 1.9 L) was added dropwise at 40° C. Then, the contents were concentrated under reduced pressure until the liquid volume reached 38 L, and propyl acetate (181 L) was added dropwise at 40° C. After stirring at 25° C. for 18 hours, the precipitated solid was collected by filtration, washed with a propyl acetate/1-propanol solution (propyl acetate 51.3 L, 1-propanol 5.7 L), and dried under reduced pressure at 40° C. to obtain the target compound (2) (18.15 kg, yield 94.7%) as a solid. $^1$H NMR (500 MHZ, DMSO-d$_6$): δ=2.21 (s, 3H), 3.25 (d, J=3.5 Hz, 2H), 7.16 (d, J=8.0 Hz, 1H), 7.38 (d, J=8.0 Hz, 1H), 8.16 (s, 1H).

Reference Example 2

Production of potassium (5-methylpyridine-2-yl) acetate (2)

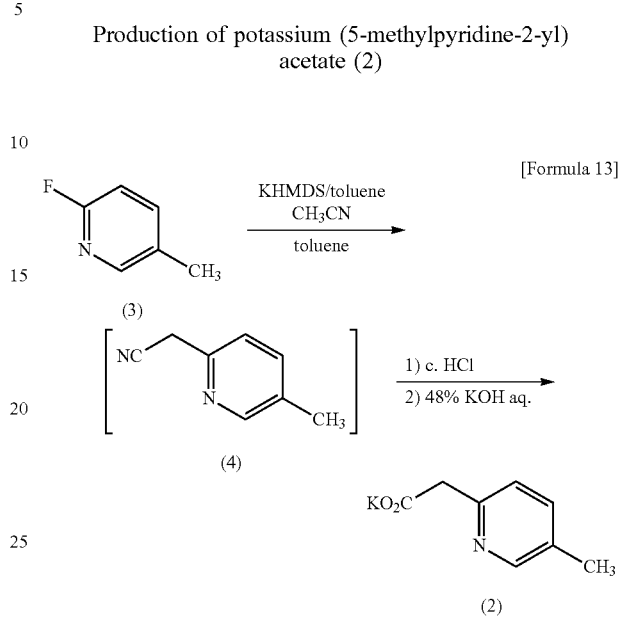

[Formula 13]

Toluene (315 mL), 2-fluoro-4-methylpyridine (3) (45 g, 405 mmol) and acetonitrile (20.0 g, 487 mmol) were added to a reaction vessel under a nitrogen atmosphere, and the contents were stirred at 0° C. A toluene solution of potassium hexmethyldisilazide (0.5 mol/L, 1.78 L, 890 mmol) was slowly added dropwise while keeping the temperature between 0° C. and 10° C. After stirring at 25° C. for one hour, the contents were stirred at 50° C. for another six hours. After cooling to 5° C., water (450 mL) was added, and the contents were stirred for 30 minutes. The liquid was separated at 5° C. and the aqueous layer was discarded. A 2N aqueous hydrochloric acid solution (522 mL) was added to the organic layer to adjust the pH to 2.4. After raising the temperature to 25° C. and stirring for 15 minutes, the pH was adjusted to 8.7 using a 4N aqueous sodium hydroxide solution. After stirring at 25° C. for 15 minutes, the aqueous layer was discarded and 135 mL of concentrated hydrochloric acid was added at 5° C. The contents were stirred at 25° C. for 15 minutes and the organic layer was discarded. The aqueous layer was heated to 80° C. and stirred for four hours. After adding 48% potassium hydroxide aqueous solution (204 g) while keeping the temperature between −5° C. and 25° C., the contents were stirred at 25° C. for 45 minutes. Next, 1-propanol (450 mL) was added and concentrated under reduced pressure until the liquid volume reached 225 mL. A 48% aqueous potassium hydroxide solution (11.8 g) was added to adjust the pH to 11.8, 1-propanol (450 mL), and the contents were concentrated under reduced pressure until the liquid volume reached 225 mL. Then, 1-propanol (450 mL) was added, the contents were concentrated under reduced pressure until the liquid volume reached 338 mL, and 1-propanol (338 mL) was added. The temperature was raised to 50° C., hot filtration was performed at the same temperature, and the contents were washed with 1-propanol (135 mL) at 50° C. to remove insoluble matter. After cooling to 25° C. and confirming crystallization, the contents were concentrated until the liquid volume reached 135 mL. Then, 585 mL of propyl acetate was added dropwise at 50° C. After stirring at 25° C. for eight hours, the precipitated solid was collected by filtration, washed with propyl acetate/1-propanol solution (propyl acetate 122 mL, 1-propanol 13.5 mL), and dried under reduced pressure at 40° C. to obtain the target compound (2) (68.9 g, yield 89.9%) as a solid.

Reference Example 3

Production of potassium (5-methylpyridine-2-yl) acetate (2)

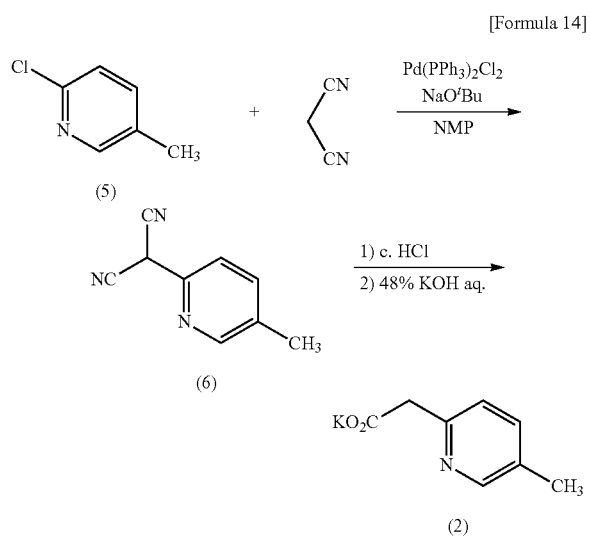

[Formula 14]

(Step 1) Production of (5-methylpyridine-2-yl) propanedinitrile (6)

Under a nitrogen atmosphere, N-methylpyrrolidone (7 L) and malononitrile (797 g, 12.1 mol) were added to a reaction vessel, and sodium tert-butoxide (2.64 kg, 27.4 mol) was added in four portions. Next, 2-chloro-4-methylpyridine (5) (1.40 kg, 11.0 mol) was added, and the oxygen concentration in the solution was lowered by aeration with nitrogen. Bis (triphenylphosphine) palladium dichloride (77.0 g, 0.11 mol) was added, and the contents were stirred at 55° C. for 1.5 hours and then at 80° C. for one hour. After cooling to 50° C., an aqueous acetic acid solution (1.0 kg acetic acid, 2.1 kg water) was added dropwise at the same temperature, and more water (18.9 kg) was added while stirring. After cooling to 25° C., the pH was adjusted to 5.6 with a 6N aqueous hydrochloric acid solution (0.95 kg). After stirring for another hour, the precipitated solid was collected by filtration, washed with N-methylpyrrolidone aqueous solution (1.4 L N-methylpyrrolidone, 4.2 L water) and then with water (5.6 L), and dried under reduced pressure at 40° C. to obtain the target compound (6) (1.67 kg, yield 96.7%) as a solid.

$^1$H NMR (500 MHZ, DMSO-d$_6$): δ=2.15 (s, 3H), 7.04 (d, J=9.0 Hz, 1H), 7.63-7.66 (m, 2H), 12.85 (brs, 1H).

(Step 2) Production of potassium (5-methylpyridine-2-yl) acetate (2)

Under a nitrogen atmosphere, concentrated hydrochloric acid (150 mL) was stirred at 40° C., and (5-methylpyridine-2-yl) propandinitrile (6) (50 g, 318 mmol) was added in five portions every hour. After the addition was completed, the contents were stirred at 40° C. for one hour and then at 80° C. for 1.5 hours. A 48% potassium hydroxide aqueous solution (241.7 g) was added while keeping the temperature between −5° C. and 10° C., the temperature was raised to 25° C., and then water (50 mL) was added. After raising the temperature to 50° C., hot filtration was performed, and the contents were washed with water (75 mL) at 50° C. to remove insoluble matter. The resulting solution was concentrated under reduced pressure until the liquid volume reached 250 mL, and 1-propanol (500 mL) was added dropwise at 45 to 50° C. After adjusting the pH to 12.6 with concentrated hydrochloric acid (12.4 mL), the contents were concentrated under reduced pressure until the liquid volume reached 250 mL, and 1-propanol (500 mL) was added dropwise at 45 to 50° C. The contents were concentrated again under reduced pressure until the liquid volume reached 250 mL, and 1-propanol (500 mL) was added dropwise at 45 to 50° C. Hot filtration was performed at 50° C. and the contents were washed with 1-propanol (150 mL) at 50° C. to remove insoluble matter. Water (50 mL) was added to the filtrate, and the contents were concentrated under reduced pressure until the volume reached 200 mL. Propyl acetate (400 mL) was added at 40° C. and the contents were concentrated under reduced pressure until the liquid volume reached 200 mL. Once again, propyl acetate (400 mL) was added at 40° C. and the contents were concentrated under reduced pressure until the liquid volume reached 200 mL. The concentrate was cooled to 25° C. and stirred for another hour, and the precipitated solid was collected by filtration, washed with a propyl acetate/1-propanol solution (135 mL propyl acetate, 15 mL 1-propanol), and dried at 40° C. under reduced pressure to obtain the target compound (2) (57.05 g, yield 94.8%) as a solid.

Reference Example 4

Production of 5-methyl-4'-oxo-1'-(tetrahydro-2H-pyran-4-ylmethyl)-1',4'-dihydro-2,3'-bipyridine-5'-ethyl carboxylate (9)

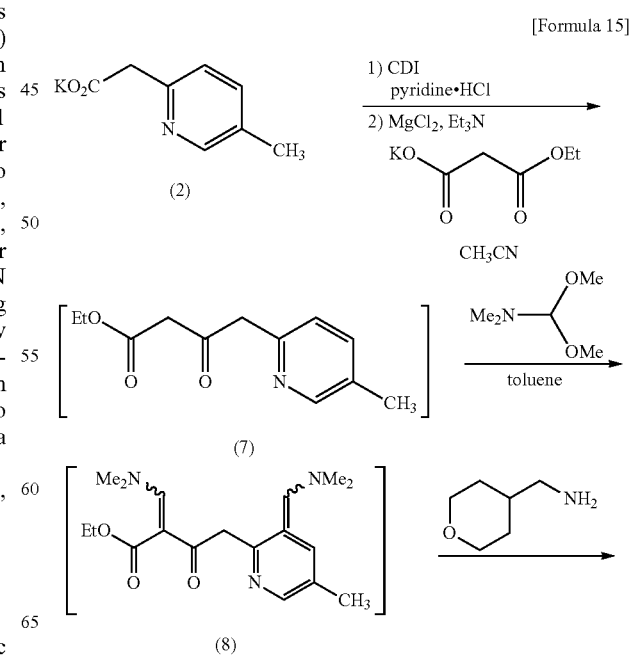

[Formula 15]

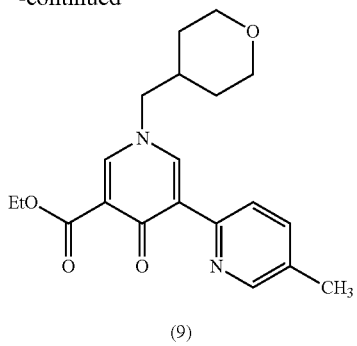

(9)

Under a nitrogen atmosphere, acetonitrile (257 L) and potassium (5-methylpyridine-2-yl) potassium acetate (2) (17.15 kg, 90.6 mol) were added to a reaction vessel, and the contents were heated under reflux at 82° C. for two hours. The contents were concentrated at atmospheric pressure until the liquid volume reached 86 L, and acetonitrile (171.5 L) was added at 25° C. Pyridine hydrochloride (12.57 kg, 109 mol) was added at 0° C. and stirred for 30 minutes, and carbonyldiimidazole (16.16 kg, 100 mol) was added at 0° C. and stirred for 40 minutes. Next, ethyl potassium malonate (23.14 kg, 136 mol) and triethylamine (18.34 kg, 181 mol) were added at 0° C., and magnesium chloride (12.08 kg, 127 mol) was added in ten portions. After stirring at 0° C. for one hour, the contents were stirred at 55° C. for another hour. Toluene (137.2 L) and water (51.5 L) were added, and the pH was adjusted to 5.01 with a 6N hydrochloric acid aqueous solution. After discarding the aqueous layer, the contents were washed twice with a 10% aqueous sodium chloride solution (51.5 L). The organic layer was concentrated under reduced pressure until the liquid volume reached 69 L, toluene (85.8 L) was added, and the contents were concentrated again under reduced pressure until the liquid volume reached 69 L. This was used as the solution of ethyl 4-(5-methylpyridine-2-yl)-3-oxobutanoate (7) in the next reaction. Under a nitrogen atmosphere, N, N-dimethylformamide dimethylacetal (76.8 kg, 645 mol) was added to another reaction vessel and the temperature was adjusted to 60° C. The solution of ethyl 4-(5-methylpyridine-2-yl)-3-oxobutanoate (7) was desalted, filtered, and added to the reaction vessel at 60° C. The contents were washed with toluene (17.2 L) and stirred at 60° C. for two hours. Next, the contents were concentrated under reduced pressure until the liquid volume reached 86 L, and the operation of adding toluene (85.8 L) was repeated four times. The contents were concentrated again under reduced pressure until the liquid volume reached 86 L, and 1-(tetrahydro-2H-pyran-4-yl) methaneamine (10.44 kg, 90.6 mol) was added at 25° C. After stirring at 25° C. for four hours, seed crystals (9) (2 g) were added. After confirming crystallization, the contents were cooled to −5° C. and stirred for 16 hours. The precipitated solid was collected by filtration, washed with toluene (51.5 L), cooled to −5° C., and dried under reduced pressure at 40° C. to obtain the target compound (9) (17.84 kg, yield 55.2%) as a solid.

The seed crystals (9) were obtained by collecting some of the reaction solution and concentrating it under reduced pressure.

$^1$H NMR (500 MHz, DMSO-d$_6$): δ=1.24-1.29 (m, 5H), 1.42-1.45 (m, 2H), 1.99-2.02 (m, 1H), 2.32 (s, 3H), 3.26 (dd, J=10.0, 10.0 Hz, 2H), 3.85 (dd, J=11.5, 3.0 Hz, 2H), 4.01 (d, J=7.5 Hz, 2H), 4.22 (q, J=7.0 Hz, 2H), 7.63 (dd, J=7.5, 2.5 Hz, 1H), 8.29 (d, J=2.5 Hz, 1H), 8.43 (s, 1H), 8.44 (s, 1H), 8.49 (d, J=2.5 Hz, 1H).

Reference Example 5

Production of 5-methyl-4'-oxo-1'-(tetrahydro-2H-pyran-4-ylmethyl)-1',4'-dihydro-2,3'-bipyridine-5'-ethyl carboxylate (9)

[Formula 16]

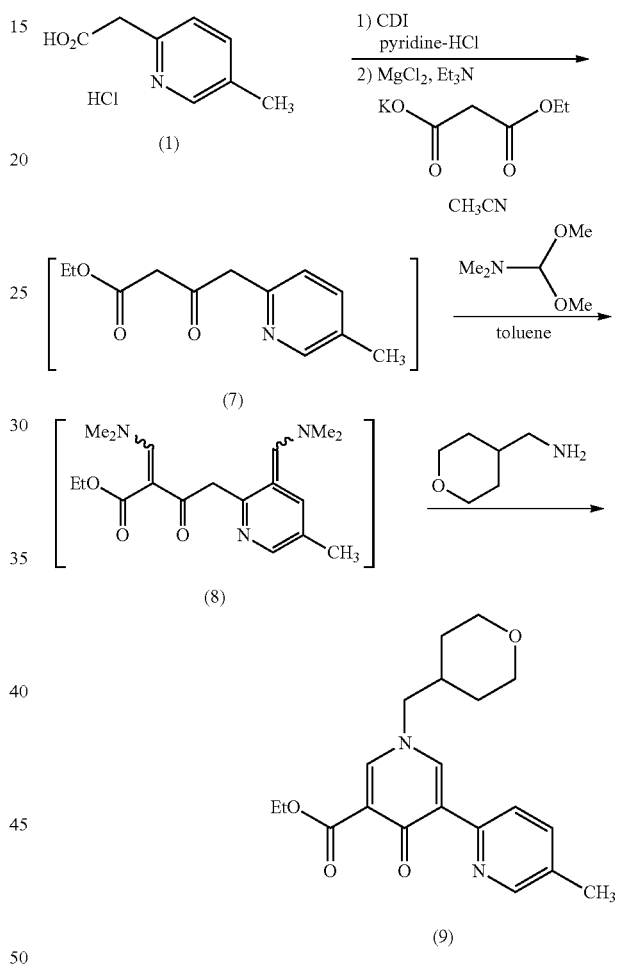

Under a nitrogen atmosphere, acetonitrile (97.5 mL) and (5-methylpyridine-2-yl) acetate monohydrochloride (1) (6.5 g, 0.035 mol) were added to a reaction vessel, triethylamine (2.74 g, 0.027 mol) was added at 0° C. and the contents were stirred for 30 minutes, and then carbonyldiimidazole (6.18 g, 0.038 mol) was added at 0° C. and the contents were stirred for one hour. Next, ethyl potassium malonate (8.84 g, 0.052 mol) and triethylamine (7.01 g, 0.069 mol) were added at 0° C., and magnesium chloride (4.62 g, 0.049 mol) was added in ten portions. After stirring at 0° C. for one hour, the contents were stirred at 57° C. for two hours. Toluene (52 mL) and water (20 mL) were added, and the pH was adjusted to about 5 with a 5N hydrochloric acid aqueous solution. The liquid was separated at about 50° C., the aqueous layer was discarded, and the contents were washed with a 10% aqueous sodium chloride solution (20 mL). The liquid was then separated at 50° C., the aqueous layer was discarded, the contents were cooled to room temperature, 32.5 mL of a 2N hydrochloric acid aqueous solution was added, and the contents were stirred for about 5 minutes. After discarding the separated organic layer, 32.5 mL of toluene was added, the pH was adjusted to about 5 with a 25% aqueous sodium chloride solution, and the contents were stirred for about five minutes. Toluene (20 mL) was added to the separated aqueous layer, and the contents were stirred for about 5 minutes. After discarding the aqueous layer, the organic layers were combined and concentrated under reduced pressure until the liquid volume reached 26 mL, toluene (32.5 mL) was added, and the contents were again concentrated under reduced pressure until the liquid volume reached 26 mL. This was used as the solution of ethyl 4-(5-methylpyridine-2-yl)-3-oxobutanoate (7) in the next reaction.

Under a nitrogen atmosphere, N, N-dimethylformamide dimethylacetal (29.12 g, 0.244 mol) was added to another reaction vessel and the temperature was adjusted to 60° C. The solution of 4-(5-methylpyridine-2-yl)-3-oxobutanoate ethyl (7) was desalted, filtered, and added dropwise to the reaction vessel at 60° C. for about one hour. The contents were washed with toluene (6.5 mL) and stirred at 60° C. for two hours. Next, the contents were concentrated under reduced pressure until the liquid volume reached 32.5 mL, and the operation of adding toluene (32.5 L) was repeated four times. The contents were concentrated again under reduced pressure until the liquid volume reached 32.5 mL, and 1-(tetrahydro-2H-pyran-4-yl) methaneamine (3.96 g, 0.034 mol) was added at 25° C. After stirring at 25° C. for four hours, seed crystals (9) (7 mg) were added. After confirming crystallization, the contents were cooled to −5° C. and stirred overnight. The precipitated solid was collected by filtration, washed with toluene (20 mL), cooled to −5° C., and dried under reduced pressure at 40° C. to obtain the target compound (9) (5.87 kg, yield 47.5%) as a solid.

The seed crystals (9) were obtained by collecting some of the reaction solution and concentrating it under reduced pressure.

Reference Example 6

Production of 5-methyl-4'-oxo-1'-(tetrahydro-2H-pyran-4-ylmethyl)-1', 4'-dihydro-2,3'-bipyridine-5'-carboxylic acid (10)

[Formula 17]

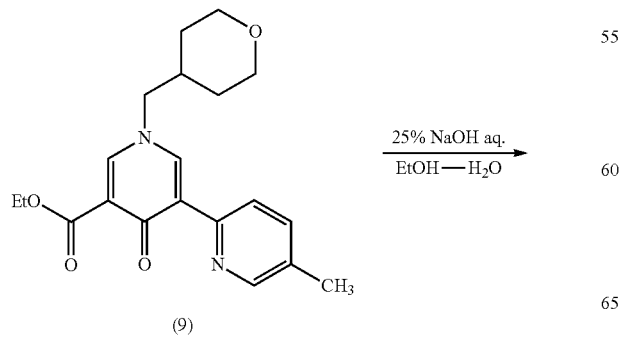

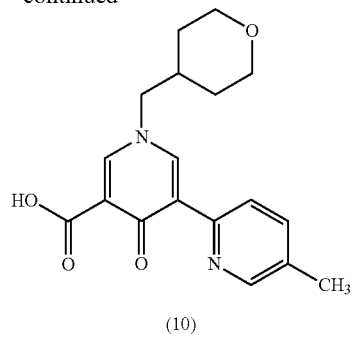

Under a nitrogen atmosphere, ethanol (50 mL), water (225 mL), 5-methyl-4'-oxo-1'-(tetrahydro-2H-pyran-4-ylmethyl)-1', 4'-dihydro-2,3'-bipyridin-5'-ethyl carboxylate (9) (50 g, 14.0 mmol), and a 25% sodium hydroxide aqueous solution (26.9 g, 16.8 mmol) were added to a reaction vessel, and the contents were stirred at 25° C. for two hours. Toluene (150 mL) and water (50 mL) were added, and the organic layer was discarded. Ethanol (185 mL) was added to the aqueous layer, and the pH was adjusted to 4.8 with a 6N aqueous hydrochloric acid solution (28 mL). After stirring at 25° C. for another 30 minutes, the precipitated solid was collected by filtration, washed with an aqueous ethanol solution (75 mL of ethanol, 75 mL of water) and then with water (150 mL), and dried under reduced pressure at 40° C. to obtain the target (10) (42.93 g, yield 93.1%) as a solid.

$^1$H NMR (500 MHZ, DMSO-d$_6$): δ=1.29-1.33 (m, 2H), 1.43-1.45 (m, 2H), 2.06-2.07 (m, 1H), 2.36 (s, 3H), 3.27 (dd, J=10.0, 9.5 Hz, 2H), 3.84 (dd, J=11.5, 2.5 Hz, 2H), 4.23 (d, J=7.5 Hz, 2H), 7.72 (dd, J=8.0, 2.5 Hz, 1H), 8.38 (d, J=8.0 Hz, 1H), 8.53 (d, J=2.5 Hz, 1H), 8.78 (s, 1H), 8.84 (s, 1H).

Reference Example 7

Production of (2-fluoro-4-nitrophenyl) acetonitrile (13)

[Formula 18]

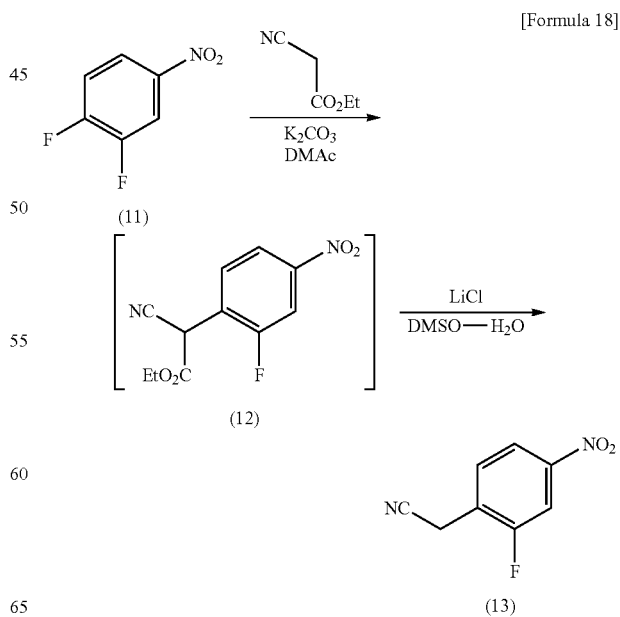

Under a nitrogen atmosphere, N,N-dimethylacetamide (5.00 L) was stirred at 25° C., potassium carbonate (0.956 kg, 6.92 mol), 1,2-difluoro-4-nitrobenzene (11) (1.00 kg, 6.29 mol), and ethyl cyanoacetate (0.782 kg, 6.91 mol) were added, and the temperature was raised to 90° C. After stirring at the same temperature for four hours, the contents were cooled to 25° C. Water (3.50 L) was added dropwise to the solution over 30 minutes, a 2N hydrochloric acid aqueous solution (6.91 L) added dropwise over 15 minutes, and then ethyl acetate (10.0 L) was added. After stirring the contents at 25° C. for five minutes and then allowing them to stand, the aqueous layer was discarded. Water (8.50 L) and sodium chloride (1.50 kg) were added to the organic layer, the contents were stirred at 25° C. for 5 minutes and allowed to stand, and then the aqueous layer was discarded. The resulting organic layer was concentrated under reduced pressure to a liquid volume of 3.0 L, and dimethyl sulfoxide (2.50 L) was added. After concentrating the solution under reduced pressure to a liquid volume of 4.0 L, a mixture of water (1.50 L) and lithium chloride (0.400 kg) was added. After raising the temperature to 100° C., the contents were stirred at the same temperature for five hours and cooled to 50° C. After adding methanol (5.00 L) to the solution, water (2.00 L) was added dropwise over 10 minutes, and then seed crystals (13) (1.00 g) were added to precipitate crystals. After confirming crystal precipitation, the contents were stirred at 50° C. for 30 minutes, and water (2.50 L) was added dropwise over one hour. After stirring at the same temperature for one hour, the contents were cooled to 25° C. over another hour. Then, the temperature was raised to 50° C., and water (4.50 L) was added dropwise over 45 minutes. After stirring at the same temperature for 30 minutes, the contents were cooled to 25° C. over one hour. After stirring at the same temperature for one hour, the precipitated solid was collected by filtration, washed with a water/methanol solution (3.00 L of water, 1.00 L of methanol), and dried under reduced pressure at 50° C. to obtain the target compound (1.05 kg, yield 92.8%) as a solid.

The seed crystals (13) were obtained by collecting some of the reaction solution and concentrating it under reduced pressure.

$^1$H NMR (500 MHZ, CDCl$_3$): δ=3.89 (s, 2H), 7.71 (dd, J=8.5, 8.0 Hz 1H), 8.01 (dd, J=2.0, 8.5 Hz, 1H), 8.12 (dd, J=8.0, 2.0 Hz, 1H).

Reference Example 8

Production of (2R)-1,4-dioxan-2-ylmethyl-methanesulfonate (17)

[Formula 19]

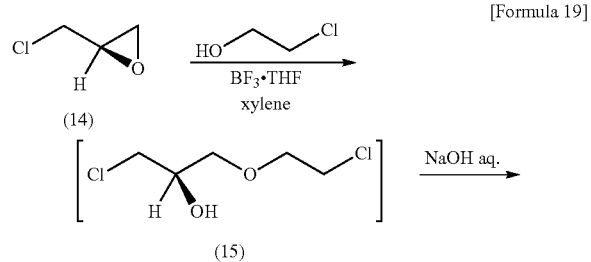

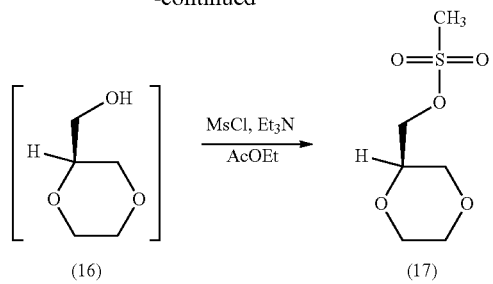

(Step 1) Production of (2S)-1,4-dioxan-2-yl methanol (16)

In a nitrogen atmosphere, 2-chloroethanol (210.0 kg) and boron trifluoride tetrahydrofuran (0.26 kg, 1.86 mol) were added to a reaction vessel, and the contents were stirred and heated to 75° C. (R)-Epichlorohydrin (14) (35.00 kg, 378.3 mol) was added dropwise over one hour and xylene (17.5 L) was added. After stirring at 75° C. for 1.5 hours, the contents were concentrated under reduced pressure to a liquid volume of 70 L. Xylene (105.0 L) was added to the solution, and the contents were concentrated again under reduced pressure to a liquid volume of 70 L. The operation of adding xylene and concentrating under reduced pressure was repeated a total of 3 times. The resulting concentrate was cooled to 15° C. and a 25% (w/w) sodium hydroxide aqueous solution (302.64 kg, 1.89 kmol) was added. The temperature was raised to 65° C., and the contents were stirred at the same temperature for 5.5 hours and then cooled to 25° C. Toluene (105.0 L) was added to the solution, the contents were stirred at 25° C. for five minutes and allowed to stand, and then the organic layer was discarded. Again, toluene (105.0 L) was added to the aqueous layer, the contents were stirred at 25° C. for five minutes and allowed to stand, and the organic layer was discarded. Concentrated hydrochloric acid (127.89 kg) was added to the resulting aqueous layer, and the pH was adjusted to 7.2. 1-Propanol (175.0 L) was added to the solution, and the contents were concentrated under reduced pressure to a liquid volume of 350 L. 1-Propanol (210.0 L) was added to the solution, and the contents were concentrated under reduced pressure to a liquid volume of 290 L. 1-Propanol (297.5 L) was added to the solution, and the contents were concentrated under reduced pressure to a liquid volume of 210 L. 1-Propanol (367.5 L) was added to the solution, and the contents were concentrated under reduced pressure to a liquid volume of 175 L. 1-Propanol (70.0 L) was added to the solution, and the contents were concentrated under reduced pressure to a liquid volume of 175 L. The suspension obtained by concentration was filtered using 1-propanol (175.0 L) to remove the precipitated inorganic salts. The resulting filtrate was concentrated under reduced pressure to a liquid volume of 30 L, and toluene (52.5 L) was added. The suspension was filtered using toluene (17.5 L) to remove precipitated inorganic salts. The resulting filtrate was concentrated under reduced pressure to a liquid volume of 30 L, and toluene (70.0 L) was added. The contents were concentrated further under reduced pressure to a liquid volume of about 20 L to obtain the target compound (16) (22.47 kg, yield 45.3%).

$^1$H NMR (500 MHZ, DMSO-d$_6$): δ=3.26 (dd, J=10.0, 11.5 Hz, 1H), 3.25-3.49 (m, 4H), 3.54 (ddd, J=2.5, 11.0, 11.5

Hz, 1H), 3.62 (dd, J=2.5, 11.5 Hz, 1H), 3.68 (dd, J=3.0, 11.5 Hz, 1H), 3.73 (dd, J=2.5, 11.0 Hz, 1H), 4.68 (t, J=5.5 Hz, 1H).

(Step 2) Production of (2R)-1,4-dioxan-2-ylmethyl-methanesulfonate (17)

The resulting (2S)-1,4-dioxane-2-ylmethanol (16) (22.00 kg, 186.2 mol) was added to another reaction vessel. Then, ethyl acetate (440.0 L), triethylamine (26.57 kg, 262.6 mol), and methanesulfonyl chloride (32.64 kg, 284.9 mol) were added, and the contents were stirred at 30° C. for one hour. Water (112.2 L) was added to the solution, the contents were stirred at 25° C. for 15 minutes and allowed to stand, and then the aqueous layer was discarded. The resulting organic layer was concentrated under reduced pressure to a liquid volume of 40 L. Methanol (68.2 L) was added to the solution, and the solution concentrated under reduced pressure to a liquid volume of 40 L. Again, methanol (68.2 L) was added to the solution, and the solution concentrated under reduced pressure to a liquid volume of 40 L. Methanol (220.0 L) was added to the solution, the solution was cooled to 5° C., and seed crystals (17) (1 g) were added to precipitate crystals. After crystal precipitation, the contents were stirred at 5° C. for one hour. After cooling to −15° C. over 2 hours, the contents were stirred at the same temperature for 24 hours. The precipitated solid was collected by filtration, washed with methanol (88.0 L), cooled to −15° C., and dried under reduced pressure at 25° C. to obtain the target compound (17) (21.19 kg, yield 63.6%) as a solid.

The seed crystals (17) were obtained by collecting some of the reaction solution and concentrating it under reduced pressure.

$^1$H NMR (500 MHz, DMSO-$d_6$): δ=3.07 (s, 3H), 3.46 (dd, J=10.0, 11.5 Hz, 1H), 3.62 (dt, J=3.0, 11.0 Hz, 1H), 3.70-3.92 (m, 5H), 4.16-4.25 (m, 2H).

Reference Example 9

Production of 4-[(2R)-1,4-dioxan-2-ylmethoxy]-3-methoxybenzaldehyde (18)

[Formula 20]

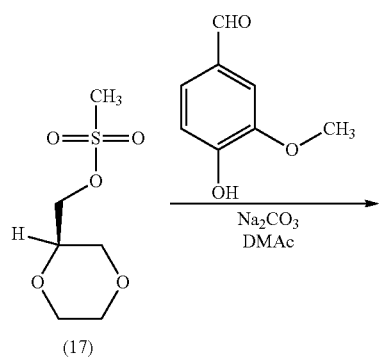

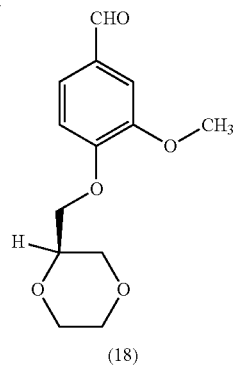

Under a nitrogen atmosphere, N,N-dimethylacetamide (45.5 L), sodium carbonate (9.96 kg, 93.97 mol), and vanillin (13.00 kg, 85.44 mol) were added, and the contents were stirred at 20° C. for 5 minutes. (2R)-1,4-Dioxan-2-ylmethyl-methanesulfonate (17) (17.60 kg, 89.70 mol) was added to the suspension, the temperature was raised to 120° C., and the contents were stirred at the same temperature for 6.5 hours. After cooling to 70° C., water (97.5 L) was added dropwise over one hour while maintaining the same temperature. Seed crystals (18) (13 g) were added to the solution to precipitate crystals. After crystal precipitation, the contents were stirred at 70° C. for one hour. Water (84.5 L) was added dropwise to the suspension over 1.5 hours while keeping the temperature at 60° C., and the contents were stirred at the same temperature for one hour. After cooling to 30° C. over one hour, the contents were stirred at the same temperature for 30 minutes. After cooling to 0° C. over another 1.5 hours, the contents were stirred at the same temperature for 15 hours. The precipitated solid was collected by filtration, washed with water (104.0 L), and dried under reduced pressure at 40° C. to obtain the target compound (18) (20.51 kg, yield 95.2%) as a solid.

The seed crystals (18) were obtained by collecting some of the reaction solution and concentrating it under reduced pressure.

$^1$H NMR (500 MHZ, DMSO-$d_6$): δ=3.40 (dd, J=10.0, 11.0 Hz, 1H), 3.47-3.53 (m, 1H), 3.60-3.70 (m, 2H), 3.74-3.79 (m, 1H), 3.80-3.86 (m, 4H), 3.87-3.93 (m, 1H), 4.03-4.10 (m, 2H), 7.19 (d, J=8.5 Hz, 1H), 7.40 (d, J=2.0 Hz, 1H), 7.53 (dd, J=2.0, 8.5 Hz, 1H), 9.84 (s, 1H).

Example 1

Production of N-benzyl-5-{4-[(2R)-1,4-dioxan-2-ylmethoxy]-3-methoxyphenyl}-3-(2-fluoro-4-nitrophenyl) pyridin-2-amine monohydrochloride (22)

[Formula 21]

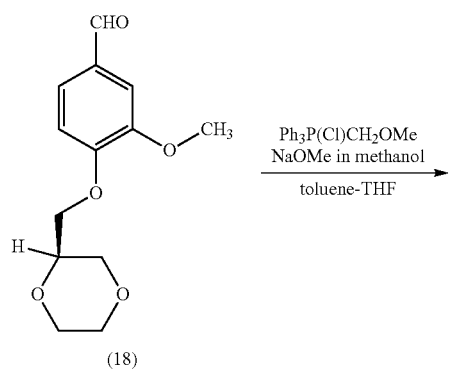

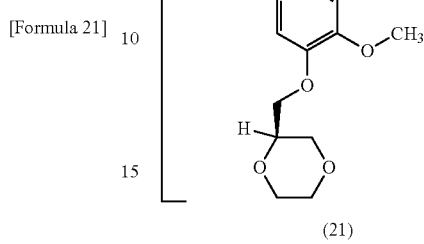

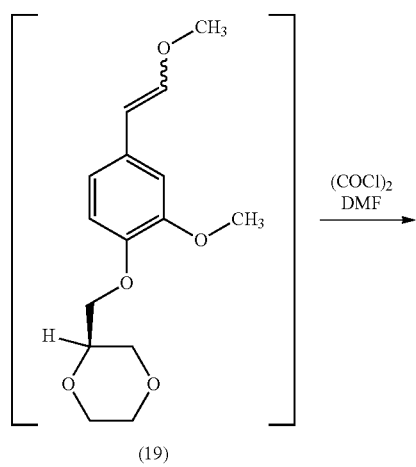

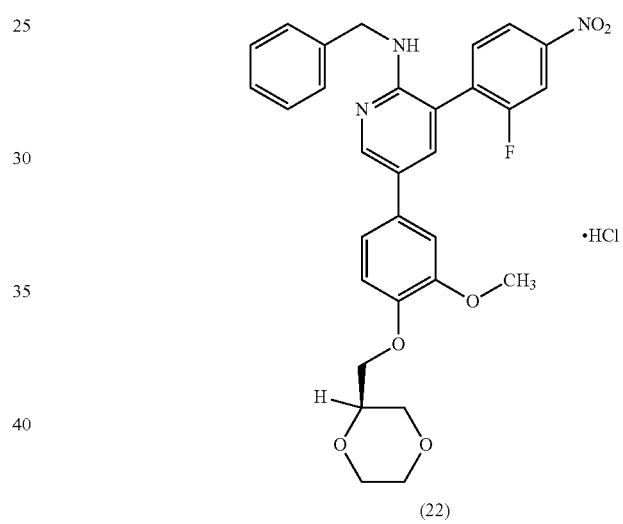

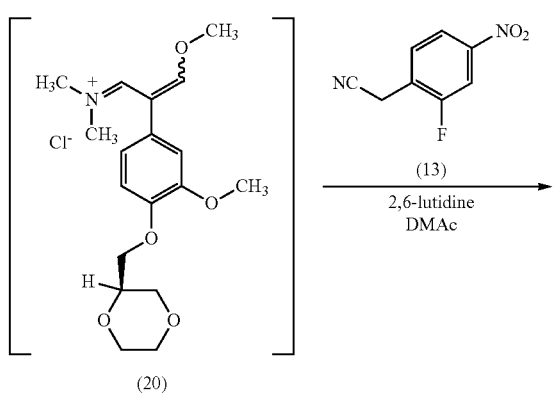

Under a nitrogen atmosphere, toluene (475 mL), 4-[(2R)-1,4-dioxan-2-ylmethoxy]-3-methoxybenzaldehyde (18) (39.0 g, 0.155 mol), and (methoxymethyl) triphenylphosphonium chloride (58.3 g, 0.17 mol) were added, and the contents were concentrated under reduced pressure to a liquid volume of 220 g. The operation of adding toluene (136 g) and concentrating the contents under reduced pressure to 135 g was carried out twice. Tetrahydrofuran (243 g) was added and the contents were cooled to 0° C. A 28% sodium methoxide/methanol solution (13.31 g, 0.185 mol) was added dropwise to the solution over 2 hours, and the contents were stirred at the same temperature for 36 hours. Water (156.0 mL) was added to the reaction solution, and the contents were stirred at 25° C. for one minute, and allowed to stand. The aqueous layer was then discarded. Water (156.0 mL) and table salt (15.6 g) were added to the organic layer, and the contents were stirred at 25° C. for 5 minutes, and allowed to stand. The aqueous layer was then discarded. The resulting organic layer was concentrated under reduced pressure until the effluent reached 477 g. Next, toluene (169.7 g) was added, and the contents were concentrated under reduced pressure again until the effluent reached 166 g. Dimethylformamide (33.9 g, 0.464 mol) and toluene (18 g) were added to the solution, and the contents were cooled to about 0° C. Then, oxalyl chloride (27.5 g, 0.217 mol) was added dropwise over 20 minutes while keeping the temperature at or below 10° C., the temperature was raised to 30° C., and the contents were stirred at the same temperature for 14 hours. After completion of the reaction, the temperature was cooled to 25° C. and a deaeration operation was performed four times. Then, the temperature was cooled to 15° C., a mixed solution of N,N-dimethylacetamide (110 g) and (2-fluoro-4-nitrophenyl) acetonitrile (13) (30.6 g, 0.17 mol) was added over 20 minutes, N,N-dimethylacetamide (147 g) was added dropwise over 20 minutes, and finally 2,6-lutidine (49.7 g, 0.464 mol) was added dropwise over 15 minutes while keeping the temperature at 15° C. The temperature was raised to 25° C., and the contents were stirred at the same temperature for 17 hours. The reaction solution was cooled to 10° C., and benzylamine (49.7 g, 0.464 mol) was added dropwise over 15 minutes while keeping the temperature at 20° C. or lower. The temperature was raised to 25° C., and the contents were stirred at the same temperature for 9 hours. After completion of the reaction, water (546 mL), methyl isobutyl ketone (468 g), and 4N sodium hydroxide aqueous solution (39 g) were added, and the contents were stirred at 25° C. for 5 minutes, and allowed to stand. The aqueous layer was then discarded. Water (585 L) was added to the organic layer, and the contents were stirred at 25° C. for 5 minutes, and allowed to stand. The aqueous layer was then discarded. Methyl isobutyl ketone (156 g) and water (156 g) were added to the obtained organic layer, the temperature was raised to 40° C., and a 7% hydrochloric acid aqueous solution (58.5 g) was added dropwise over 20 minutes while keeping the temperature at 40° C. Seed crystals (22) (39 mg) were added to the solution to precipitate crystals. After confirming crystal precipitation, the suspension was stirred at 40° C. for 30 minutes, and the pH of the suspension was adjusted to 6.67 using a 2N hydrochloric acid aqueous solution (39 g). After cooling to 25° C., the pH of the suspension was adjusted to 6.78 using a 2N hydrochloric acid aqueous solution (19.5 g). After stirring for 15 minutes or more, the precipitated solid was collected by filtration, washed with methyl isobutyl ketone (374 g), and dried under reduced pressure at 40° C. to obtain the target compound (22) (62.56 g, yield 69.5%) as a solid.

The seed crystals (22) were obtained by collecting some of the reaction solution and concentrating it under reduced pressure.

$^1$H NMR (500 MHZ, DMSO-$d_6$): δ=3.39 (dd, J=11.5, 10 Hz, 1H), 3.49 (dt, J=3, 11 Hz, 1H), 3.58-3.70 (m, 2H), 3.72-3.78 (m, 1H), 3.79-3.90 (m, 5H), 3.93-4.04 (m, 1H), 5.80 (s, 2H), 7.09 (d, J=8.5 Hz, 1H), 7.28-7.52 (m, 7H), 7.91 (dd, J=7.0, 8.0 Hz, 1H), 8.26-8.38 (m, 4H), 8.48 (d, J=2.5 Hz, 1H), 8.87 (d, J=1.5 Hz, 1H).

Example 2

Examination of production conditions for N-benzyl-5-{4-[(2R)-1,4-dioxan-2-ylmethoxy]-3-methoxyphenyl}-3-(2-fluoro-4-nitrophenyl) pyridin-2-amine monohydrochloride (22)

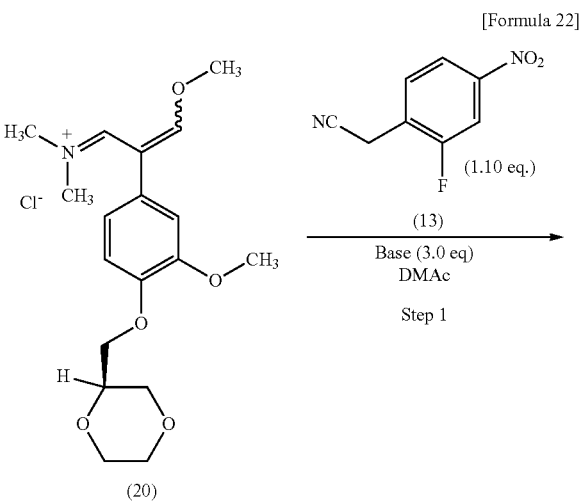

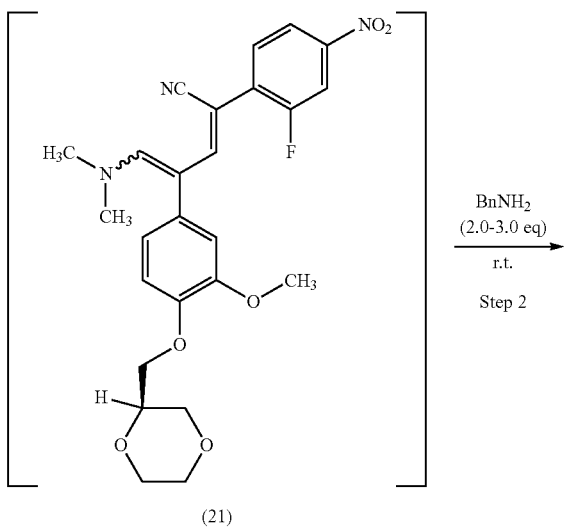

-continued

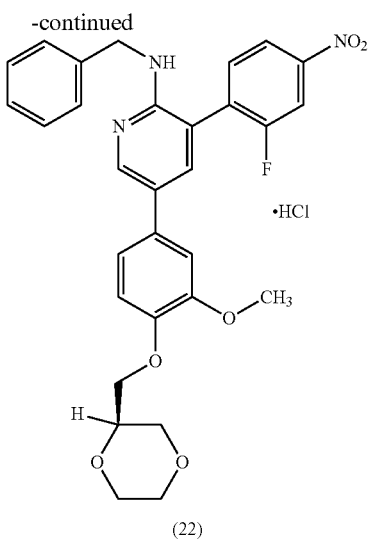

(22)

-continued

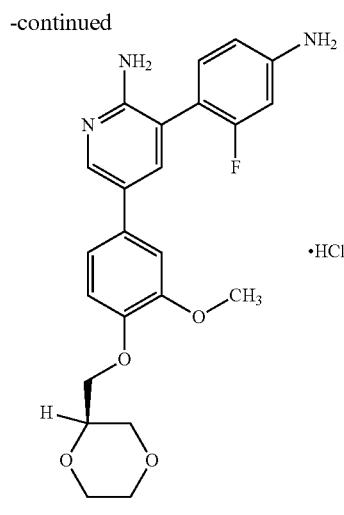

(23)

The pyridine cyclization reaction was examined using various bases in the same manner as in Example 1.

TABLE 1

| Ent. | Base | Conditions (Step1) | Yield (%) |
|---|---|---|---|
| 1 | 20% wt NaOEt/EtOH | 0° C., 1 h | 45 |
| 2 | DBU | 0° C., 3 h | 56 |
| 3 | Et3N | 0° C., 26 h | 53 |
| 4 | Pyridine | r.t., 25 h | 66 |
| 5 | 2,6-lutidine | r.t., 7 h | 72 |

Example 3

Production of 3-(4-amino-2-fluorophenyl)-5-{4-[(2R)-1,4-dioxan-2-ylmethoxy]-3-methoxyphenyl} pyridin-2-amine monohydrochloride (23)

[Formula 23]

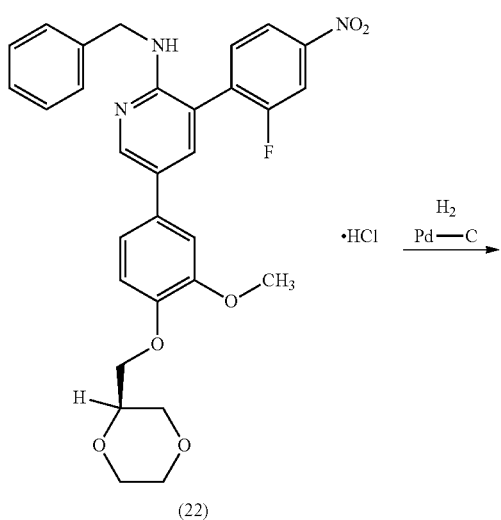

(22)

Under a nitrogen atmosphere, water (41.7 L), N-benzyl-5-{4-[(2R)-1,4-dioxan-2-ylmethoxy]-3-methoxyphenyl}-3-(2-fluoro-4)-nitrophenyl) pyridin-2-amine monohydrochloride (22) (6.95 kg, 119 mol), 1-propanol (97.3 L), and 5% Pd/C (TYPE PE, 0.76 kg) were added, and nitrogen substitution was performed three times at a pressure of 0.3 MPaG. The temperature was raised to 50° C., and hydrogen substitution was performed three times at a pressure of 0.3 MPaG. Then, the contents were stirred for two hours at a temperature of 50° C. and under 0.3 MPaG of hydrogen pressure. The temperature was raised to 70° C., the contents were stirred for seven hours, and the system was purged with nitrogen. After filtering at the same temperature to remove the catalyst, the contents were washed with a water/1-propanol solution (water 6.3 L, 1-propanol 14.6 L) at 70° C., and the resulting filtrate was cooled to 40° C. The filtrate was concentrated under reduced pressure to 52 L while keeping the temperature at 40° C., and 1-propanol (69.5 L) was added. The filtrate was concentrated under reduced pressure until the liquid volume reached 52 L once again while keeping the temperature at 40° C., and 1-propanol (52.1 L) was added. The solution was raised to 55° C. and stirred for two hours. Then, the contents were cooled to 25° C. and stirred for 18 hours, and the precipitated solid was collected by filtration, washed with 1-propanol (34.8 L), and dried under reduced pressure at 40° C. to obtain the target compound (23) (4.97 kg, yield 90.1%) as a solid.

$^1$H NMR (500 MHz, DMSO-$d_6$): δ=3.43 (dd, J=10, 11 Hz, 1H), 3.53 (dt, J=3.0, 11 Hz, 1H), 3.64-3.72 (m, 2H), 3.80 (dd, J=2.0, 11.5 Hz, 1H), 3.85-3.92 (m, 5H), 3.97-4.04 (m, 2H), 5.86 (br, 1H), 6.51 (dd, J=2.0, 12.5 Hz, 1H), 6.57 (dd, J=2.0, 8.5 Hz, 1H), 7.08 (d, J=8.5 Hz, 1H), 7.17 (t, J=8.5 Hz, 1H), 7.26 (dd, J=2.0, 8.5 Hz, 1H), 7.33 (d, J=2.0 Hz, 1H), 7.65 (br, 2H), 8.17 (d, J=2.0 Hz, 1H), 8.37 (d, J=2.0 Hz, 1H).

Example 4

Production of 3-(4-amino-2-fluorophenyl)-5-{4-[(2R)-1,4-dioxan-2-ylmethoxy]-3-methoxyphenyl} pyridin-2-amine monohydrochloride (23)

Under a nitrogen atmosphere, N-benzyl-5-{4-[(2R)-1,4-dioxan-2-ylmethoxy]-3-methoxyphenyl}-3-(2-fluoro-4-nitrophenyl) pyridin-2-amine monohydrochloride (22) (40 g, 0.069 mol), N-methylpyrrolidone (200 mL), and 5% Pd/C (TYPE PE, 4.5 g) were added, and nitrogen substitution and hydrogen substitution were performed three times each at a pressure of 0.3 MPaG. Then, the temperature was raised to 50° C., and the contents were stirred for one hour under a hydrogen pressure of 0.3 MPaG. The temperature was raised to 70° C., the contents were stirred for two hours, and then the system was purged with nitrogen. The contents were cooled to room temperature, a 50% sodium hydroxide aqueous solution (8.08 g, 0.069 mol) was added, and the contents were stirred overnight. Then, after filtering and removing the catalyst, the contents were washed with N-methylpyrrolidone (40 mL), 2-propanol (240 mL) was added at the same temperature, 6N-hydrochloric acid aqueous solution (4 g) was then added, and seed crystals (23) (40 mg) were added. After confirmation of crystallization, the contents were stirred for two hours, 2-propanol (240 mL) was added, the pH was adjusted to 3.5 with a 6N hydrochloric acid aqueous solution, and the mixture was stirred for three hours. The precipitated solid was collected by filtration, washed a first time with a mixture of N-methylpyrrolidone (28 mL) and 2-propanol (56 mL), and then washed a second time with 2-propanol (80 mL). Then, the contents were dried under reduced pressure at 40° C. to obtain the target compound (23) (29.90 kg, yield 94.2%) as a solid.

The seed crystals (23) were obtained by collecting some of the reaction solution and concentrating it under reduced pressure.

Example 5

Production of N-[4-(2-amino-5-{4-[(2R)-1,4-dioxan-2-ylmethoxy]-3-methoxyphenyl} pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide (25)

[Formula 24]

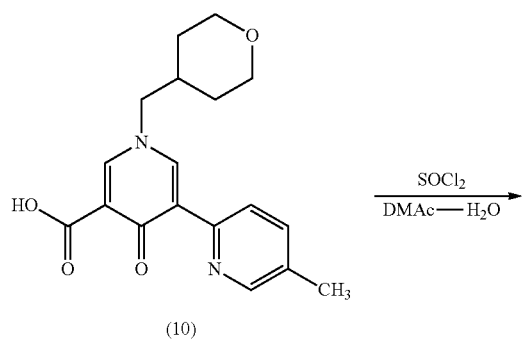

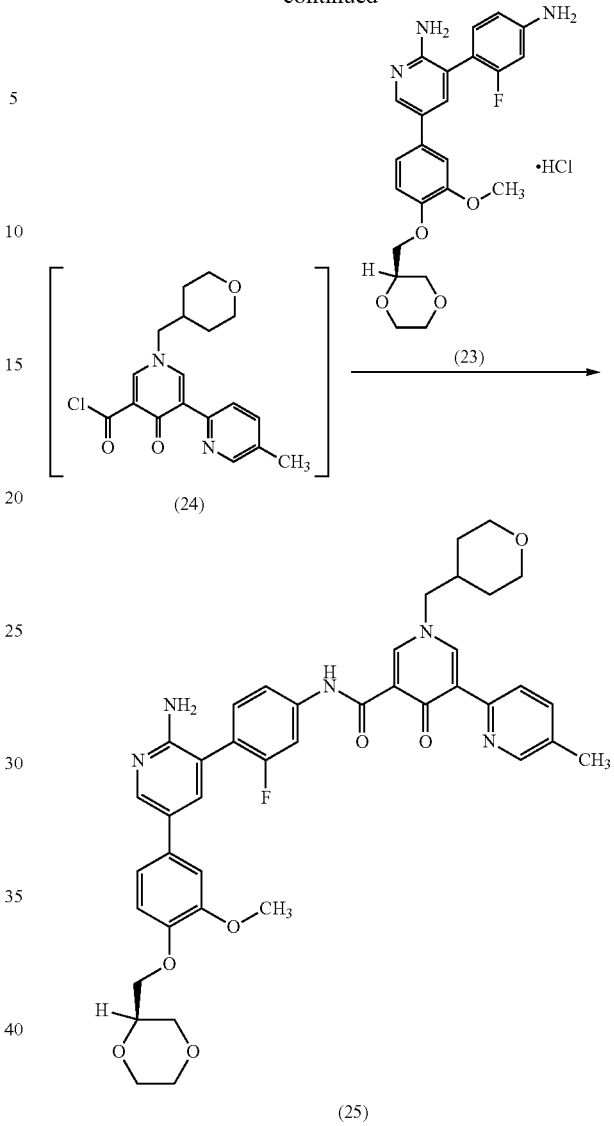

Under a nitrogen atmosphere, N,N-dimethylacetamide (35.6 L), 5-methyl-4'-oxo-1'-(tetrahydro-2H-pyran-4-ylmethyl)-1',4'-dihydro-2,3'-bipyridin-5'-carboxylic acid (10) (3.56 kg, 10.8 mol) and purified water (152 g) were added, and the contents were cooled to −8° C. Then, thionyl chloride (2.46 kg, 20.7 mol) was added dropwise over 50 minutes, and the contents were stirred at the same temperature for 1.5 hours. Next, 3-(4-amino-2-fluorophenyl)-5-{4-[(2R)-1,4-dioxan-2-ylmethoxy]-3-methoxyphenyl} pyridin-2-amine monohydrochloride (23) (4.77 kg, 10.3 mol) and N,N-dimethylacetamide (3.6 L) were added, and the contents were stirred at −8° C. for 40 hours. Then, a mixed solution of N,N-dimethylacetamide (14.3 L) and water (3.6 L) was added, and the contents were stirred at −8° C. for 1.5 hours and then heated to 60° C. After adding water (7.1 L) to the solution, the pH of the solution was adjusted to 5.5 with triethylamine. Then, seed crystals (25) (0.4 g) were added to precipitate crystals. After confirming precipitation of crystals, the contents were stirred at 60° C. for 3.5 hours, and water (16.0 L) was added dropwise over one hour while maintaining the same temperature. Triethylamine was added to the suspension to adjust the pH to 5.7, and the suspension was then cooled to 25° C. over one hour. After stirring at the same temperature for 14 hours, the precipitated solid was collected by filtration and washed with 33% N,N-dimethylacetamide aqueous solution (N,N-dimethylacetamide 11.7 L, water 23.8 L) and then normal water (35.6 L), and the contents were dried under reduced pressure at 40° C. to obtain the target compound (25) (7.17 kg, yield 94.4%).

The seed crystals (25) were obtained by collecting some of the reaction solution and concentrating it under reduced pressure.

$^1$H NMR (500 MHZ, CDCl$_3$): δ=1.42-1.62 (m, 4H), 2.16 (m, 1H), 2.40 (s, 3H), 3.39 (dt, J=2.0, 12 Hz, 2H), 3.55 (dd, J=12, 10 Hz, 1H), 3.65-3.89 (m, 4H), 3.91 (s, 3H), 3.93-4.10 (m, 8H), 4.55 (br, 2H), 6.96 (d, J=8.0 Hz, 1H), 7.03 (d, J=2.0 Hz, 1H), 7.05 (dd, J=2.0, 8.5 Hz, 1H), 7.38 (t, J=8.0 Hz, 1H), 7.50 (dd, J=2.0, 8.5 Hz, 1H), 7.59 (d, J=2.5 Hz, 1H), 7.62 (dd, J=2.5, 8.0 Hz, 1H), 7.92 (dd, J=4.0, 12 Hz, 1H), 8.31 (d, J=2.0 Hz, 1H), 8.41 (d, J=2.5 Hz, 1H), 8.47-8.48 (m, 2H), 8.56 (d, J=2.5 Hz, 1H), 13.01 (s, 1H).

Example 6

Production of N-[4-(2-amino-5-{4-[(2R)-1,4-dioxan-2-ylmethoxy]-3-methoxyphenyl} pyridin-3-yl)-3-fluorophenyl]-5-methyl-4'-oxo-1'-(tetrahydro-2H-pyran-4-ylmethyl)-1',4'-dihydro-2,3'-bipyridine-5'-carboxamide (25)

[Formula 25]

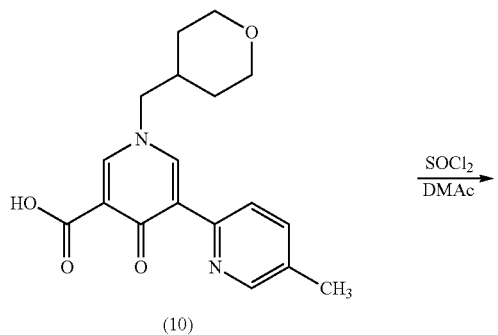

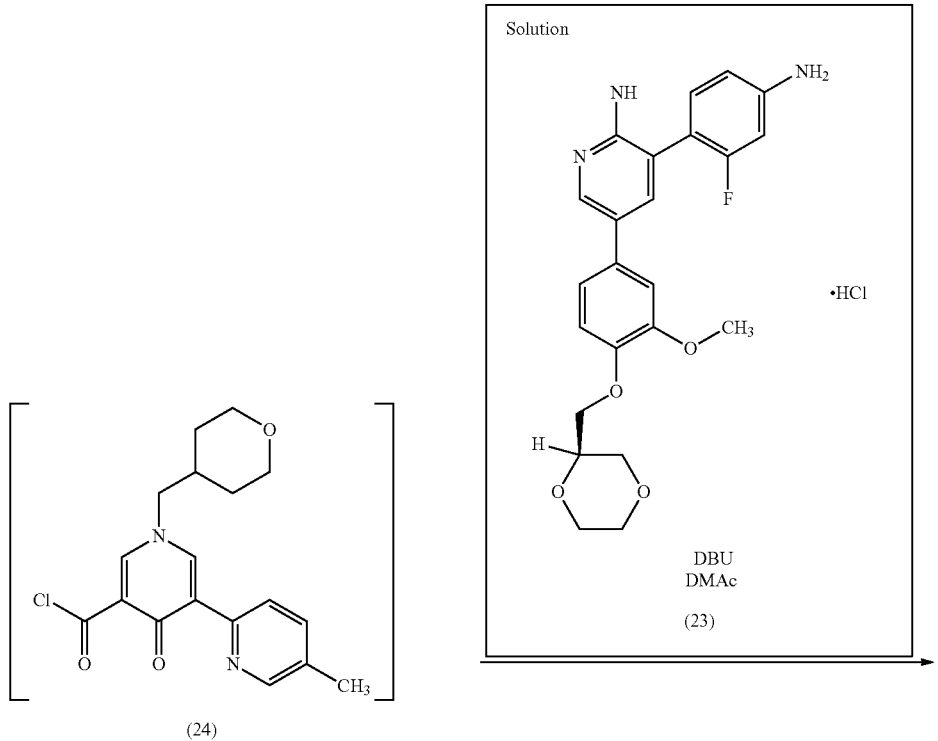

-continued

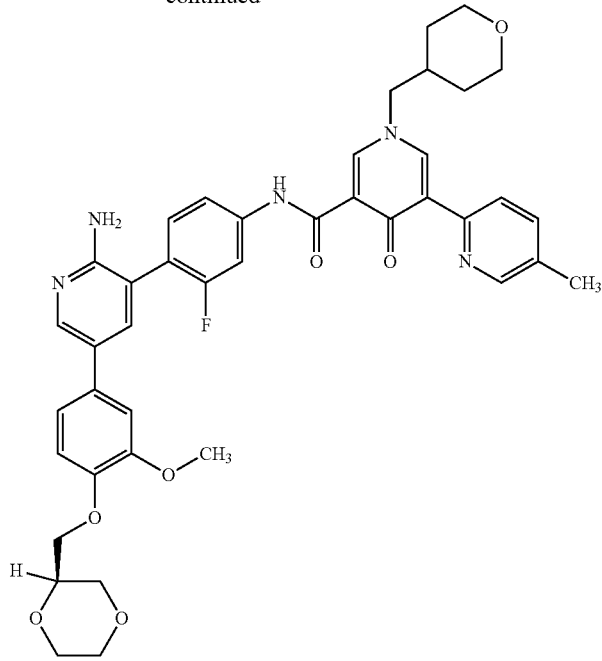

(25)

N,N-dimethylacetamide (67.5 mL) and 5-methyl-4'-oxo-1'-(tetrahydro-2H-pyran-4-ylmethyl)-1',4'-dihydro-2,3'-bipyridin-5'-carboxylic acid (10) (6.72 g, 0.020 mol) were added to reaction vessel 1 under a nitrogen atmosphere, and the contents were cooled to −10° C. Then, thionyl chloride (2.55 g, 0.021 mol) was added dropwise over 50 minutes, and the contents were stirred at the same temperature for four hours.

N, N-dimethylacetamide (49.5 mL), 3-(4-amino-2-fluorophenyl)-5-{4-[(2R)-1,4-dioxan-2-ylmethoxy]-3-methoxyphenyl} pyridin-2-amine monohydrochloride (23) (9.00 g, 0.019 mol), and 1,8-diazabicyclo [5.4.0] undeca-7-ene (DBU) (3.11 g, 0.020 mol) was added to reaction vessel 2 under a nitrogen atmosphere. After stirring at room temperature for 0.5 hours to completely dissolve the contents, the contents were cooled to −10° C.

Next, the solution in reaction vessel 2 was added dropwise to reaction vessel 1 over one hour while keeping the temperature at −10° C. After stirring at the same temperature for two hours, water (18 mL) was added and the temperature was raised to 60° C. Triethylamine was added to the solution to adjust the pH of the solution to 7.5, and then seed crystals (25) (1.0 mg) were added to precipitate crystals. After confirming precipitation of crystals, the contents were stirred at 60° C. for three hours, and water (45.0 mL) was added dropwise over one hour while maintaining the same temperature. Then, the contents were cooled to 25° C. over one hour. After stirring at the same temperature for 16 hours, the precipitated solid was collected by filtration and mixed with 33% N, N-dimethylacetamide aqueous solution (N,N-dimethylacetamide 45.2 mL, water 22.3 mL) and then normal water (67.5 mL), and the contents were washed and dried under reduced pressure at 40° C. to obtain the target compound (25) (13.55 g, yield 94.5%) as a solid.

The seed crystals (25) were obtained by collecting some of the reaction solution and concentrating it under reduced pressure.

Example 7

Production of N-[4-(2-amino-5-{4-[(2R)-1,4-dioxan-2-ylmethoxy]-3-methoxyphenyl} pyridin-3-yl)-3-fluorophenyl]-5-methyl-4'-oxo-1'-(tetrahydro-2H-pyran-4-ylmethyl)-1', 4'-dihydro-2,3'-bipyridine-5'-carboxamide sulfate hydrate (26)

Under a nitrogen atmosphere, acetone (49 mL), N-[4-(2-amino-5-{4-[(2R)-1,4-dioxan-2-ylmethoxy]-3-methoxyphenyl} pyridin-3-yl)-3-fluorophenyl]-5-methyl-4'-oxo-1'-(tetrahydro-2H-pyran-4-ylmethyl)-1',4'-dihydro-2,3'-bipyridin-5'-carboxamide (25) (10.00 g, 0.014 mol), and purified water (1.7 mL) were added, the temperature was raised to 45° C., and then a 25% sulfuric acid aqueous solution (5.87 g) was added while keeping the temperature at 45° C. After confirming dissolution of the crystals, filtration was performed at the same temperature to remove insoluble matter, and the contents were washed with a mixed solution of purified water and acetone (9 mL of purified water, 21 mL of acetone). Afterwards, a 25% sulfuric acid aqueous solution (4.27 g) was added and then seed crystals (26) (10 mg) were added to precipitate crystals. After confirming precipitation of crystals and then stirring overnight, purified water (3 mL) was added, the temperature was raised to 55° C., and the contents were stirred for one hour. After cooling to 45° C., acetone (40 mL) was added dropwise over 30 minutes. After stirring at 45° C. for 30 minutes, acetone (40 mL) was added dropwise over 30 minutes. After stirring at 45° C. for 30 minutes, acetone (40 mL) was again added dropwise over 30 minutes. After stirring at 45° C. for 30 minutes, acetone (80 mL) was added dropwise over one hour. Then, the contents were cooled to 25° C. over 60 minutes and stirred at the same temperature overnight. The precipitated solid was collected by filtration, the crystals were washed a first time with a mixed solution of acetone and purified water (44 mL of acetone, 6 mL of purified water) and a second time with acetone (50 mL), and the crystals were dried at 35° C. under reduced pressure of 3 kPa to obtain the target compound (26) (11.95 g) as a solid.

The seed crystals (26) were obtained by collecting some of the reaction solution and concentrating it under reduced pressure. A powder X-ray crystal structure analysis was performed on the resulting crystals. The results are shown in FIG. 1 and Table 2.

$^1$H NMR (500 MHz, DMSO-$d_6$): δ=1.37 (dq, J=4.0, 12 Hz, 2H), 1.52 (d, J=11.5 Hz, 2H), 2.15 (m, 1H), 2.49 (s, 1H), 3.31 (dt, J=1.5, 11.5 Hz, 2H), 3.44 (dd, J=10, 11.5 Hz, 1H), 3.53 (dt, J=1.5, 11 Hz, 1H), 3.64-3.73 (m, 2H), 3.80 (dd, J=2.0, 12 Hz, 1H), 3.85-3.92 (m, 5H), 3.98-4.05 (m, 2H), 4.26 (d, J=7.5 Hz, 2H), 7.10 (d, J=8.5 Hz, 1H), 7.30 (dd, J=2.5, 8.5 Hz, 1H), 7.36 (d, J=2.5 Hz, 1H), 7.57-7.62 (m, 2H), 7.77 (br, 2H), 8.04 (dd, J=2.0, 13 Hz, 1H), 8.11 (br, 1H), 8.38 (dd, J=2.5, 9.0 Hz, 2H), 8.48 (d, J=8.5 Hz, 1H), 8.69 (s, 1H), 8.88 (dd, 2.0, 7.0 Hz, 2H), 13.02 (br, 1H).

TABLE 2

| Peak No. | 2θ | d Value |
|---|---|---|
| 1 | 3.71 | 23.80 |
| 2 | 6.48 | 13.64 |
| 3 | 7.37 | 11.99 |
| 4 | 9.80 | 9.02 |
| 5 | 10.29 | 8.59 |
| 6 | 11.01 | 8.03 |
| 7 | 18.44 | 4.81 |
| 8 | 20.53 | 4.32 |
| 9 | 22.91 | 3.88 |
| 10 | 24.15 | 3.68 |

The invention claimed is:

1. A production method comprising the step of reacting a compound represented by Formula (I):

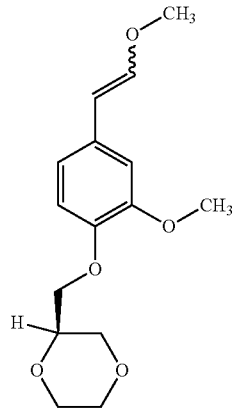

with a chlorinating agent and dimethylformamide to obtain a compound represented by Formula (II):

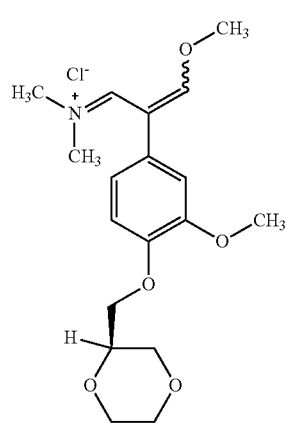

or a salt thereof.

2. The method according to claim 1, wherein the chlorinating agent is oxalyl chloride.

3. The method according to claim 1, further comprising reacting the compound represented by Formula (II) or a salt thereof with a compound represented by Formula (III):

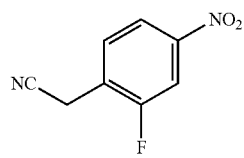

in the presence of a base to obtain a compound represented by Formula (IV):

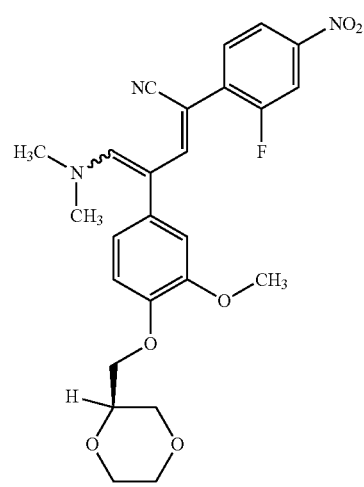

or a salt thereof.

4. The method according to claim 3, wherein the base is 2,6-lutidine.

5. The method according to claim 3, further comprising reacting the compound represented by Formula (IV) or a salt thereof with benzylamine to obtain a compound represented by Formula (V):

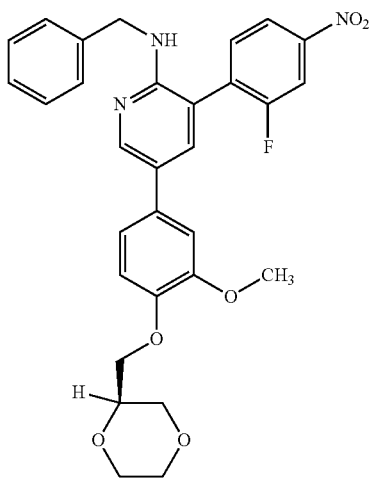

or a salt thereof.

6. A production method comprising the steps of:
(i) reacting a compound represented by Formula (I') with a Wittig reagent;

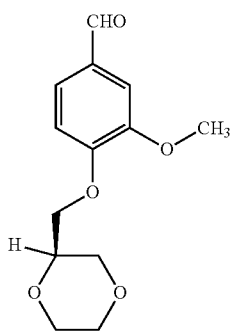

(ii) reacting the compound obtained in step (i) with a chlorinating agent and dimethylformamide;
(iii) reacting the compound obtained in step (ii) with a compound represented by Formula (III):

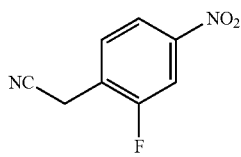

in the presence of a base; and
(iv) reacting the compound obtained in step (iii) with benzylamine to obtain a compound represented by Formula (V):

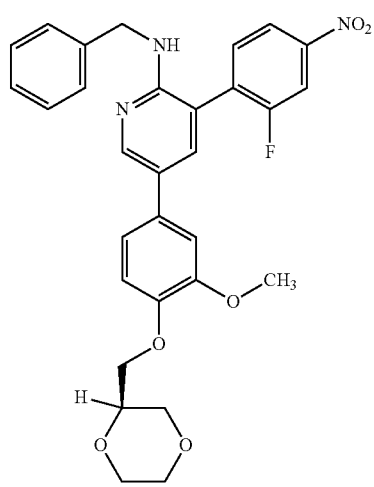

or a salt thereof.

7. The method according to claim 6, wherein the Wittig reagent in step (i) is $Ph_3P(Cl)CH_2OMe$.

8. The method according to claim 6, wherein the chlorinating agent in step (ii) is oxalyl chloride.

9. The method according to claim 6, wherein the base in step (iii) is 2,6-lutidine.

10. The method according to claim 5, further comprising reacting the compound represented by Formula (V) or salt thereof with hydrogen in a solvent and in the presence of a palladium on carbon catalyst to obtain a compound represented by Formula (VI):

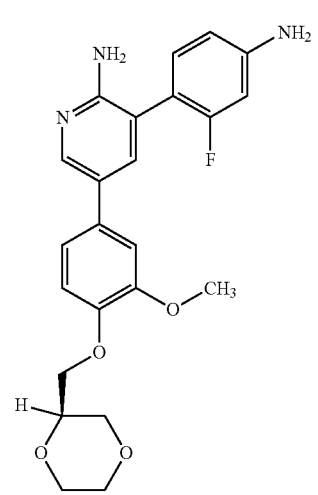

or a salt thereof.

11. The method according to claim 10, wherein the compound represented by Formula (V) or salt thereof is a hydrochloric acid salt of a compound represented by Formula (V), and the solvent is 1-propanol or N-methylpyrrolidone.

12. The method according to claim 10, further comprising condensing the compound represented by Formula (VI) or salt thereof with a compound represented by Formula (VII):

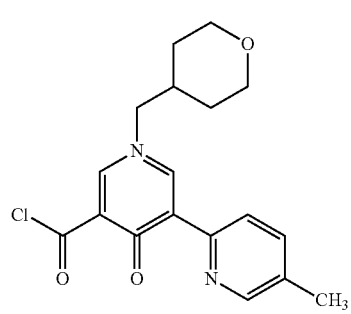

(VII)

or a salt thereof to obtain a compound represented by Formula (VIII):

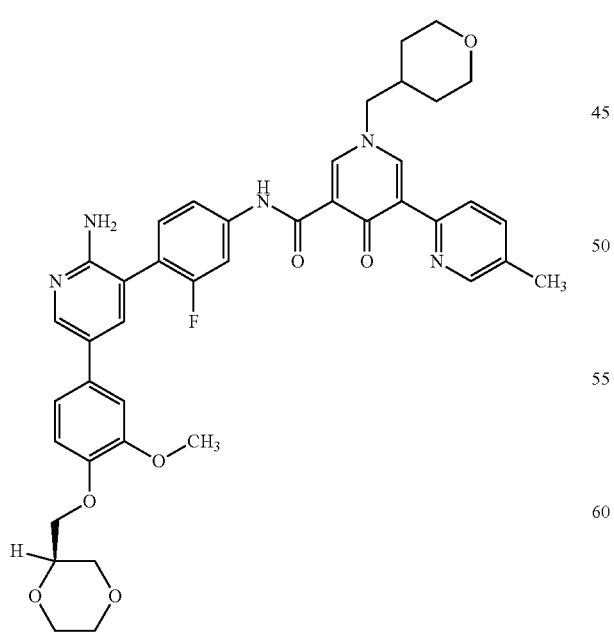

(VIII)

or a salt thereof.

13. The method according to claim 12, wherein the compound represented by Formula (VIII) or a salt thereof is a sulfuric acid salt of the compound represented by Formula (VIII).

14. A production method, comprising reacting a compound represented by Formula (VI):

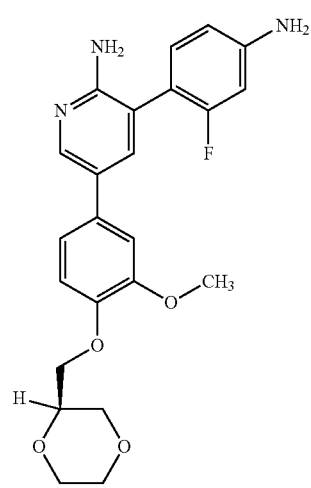

(VI)

or a salt thereof with a compound represented by Formula (VII):

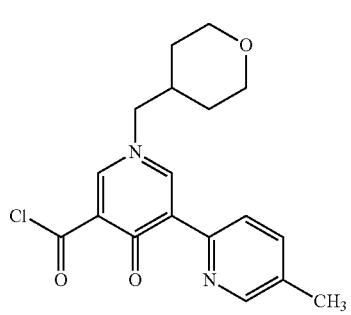

(VII)

or a salt thereof to obtain a compound represented by Formula (VIII):

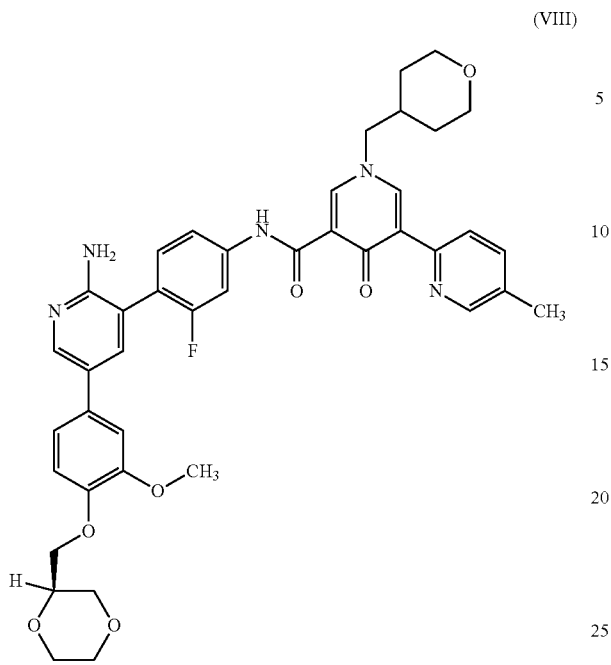

(VIII)

or a salt thereof.

15. The method according to claim 14, wherein the compound represented by Formula (VIII) or a salt thereof is a sulfuric acid salt of the compound represented by Formula (VIII).

16. The method according to claim 14, further comprising reacting a compound represented by Formula (V) or a salt thereof:

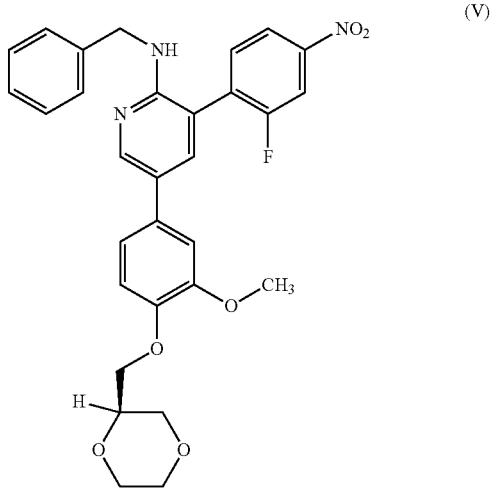 [SMILES: COc1cc(-c2cnc(NCc3ccccc3)c(-c3ccc([N+](=O)[O-])cc3F)c2)ccc1OC[C@H]1COCCO1]

(V)

with hydrogen in a solvent to obtain the compound represented by Formula (VI) or a salt thereof.

17. The method according to claim 16, wherein the compound represented by Formula (V) or salt thereof is a hydrochloric acid salt of a compound represented by Formula (V), and the solvent is 1-propanol or N-methylpyrrolidone.

18. The method according to claim 16, wherein reacting a compound represented by Formula (V) or a salt thereof with hydrogen is performed in the presence of a palladium on carbon catalyst.

* * * * *